(12) United States Patent
Coope-Epstein et al.

(10) Patent No.: US 10,066,190 B2
(45) Date of Patent: Sep. 4, 2018

(54) MILD LIQUID DETERGENT FORMULATIONS

(71) Applicant: Henkel IP & Holding GmbH, Duesseldorf (DE)

(72) Inventors: Janet Coope-Epstein, Trumbull, CT (US); Lisa Ann Young, Fishkill, CT (US); Ryan Bradley Cameron, Newtown, CT (US); Meghan Russell, Monroe, CT (US)

(73) Assignee: Henkel IP & Holding GmbH (DE)

( * ) Notice: Subject to any disclaimer, the term of this patent is extended or adjusted under 35 U.S.C. 154(b) by 0 days.

(21) Appl. No.: 15/652,845

(22) Filed: Jul. 18, 2017

(65) Prior Publication Data

US 2018/0016523 A1    Jan. 18, 2018

Related U.S. Application Data

(60) Provisional application No. 62/363,748, filed on Jul. 18, 2016.

(51) Int. Cl.
| | |
|---|---|
| *C11D 17/00* | (2006.01) |
| *C11D 1/831* | (2006.01) |
| *C11D 1/94* | (2006.01) |
| *C11D 11/00* | (2006.01) |
| *G01N 33/26* | (2006.01) |
| *C11D 1/22* | (2006.01) |
| *C11D 1/29* | (2006.01) |
| *C11D 1/66* | (2006.01) |

(Continued)

(52) U.S. Cl.
CPC ............... *C11D 1/831* (2013.01); *C11D 1/94* (2013.01); *C11D 11/0094* (2013.01); *G01N 33/26* (2013.01); *C11D 1/22* (2013.01); *C11D 1/29* (2013.01); *C11D 1/662* (2013.01); *C11D 1/72* (2013.01); *C11D 1/90* (2013.01)

(58) Field of Classification Search
CPC ............................................. C11D 17/00
USPC ......................................... 510/119
See application file for complete search history.

(56) References Cited

U.S. PATENT DOCUMENTS

| | | |
|---|---|---|
| 3,598,865 A | 8/1971 | Lew |
| 4,565,647 A | 1/1986 | Llenado |
| 5,958,864 A | 9/1999 | Artiga Gonzalez et al. |

(Continued)

FOREIGN PATENT DOCUMENTS

| | | |
|---|---|---|
| EP | 0132043 A1 | 1/1985 |
| EP | 0132046 A1 | 1/1985 |

(Continued)

OTHER PUBLICATIONS

Crawford, Charles, et al. "Summary of Laundry detergents and skin irritancy—a comprehensive review" Skinmed, vol. 12, Issue 1, 2014, pp. 1-2.

(Continued)

*Primary Examiner* — Gregory Webb
(74) *Attorney, Agent, or Firm* — Bojuan Deng

(57) ABSTRACT

The present invention provides methods for determining mild aqueous laundry detergent formulations, mild liquid laundry detergent formulations, and methods for preparing the same. The formulations comprise various surfactants and have a low detergent mildness indicator, derived from combining results from Zein test, corneosurfametry test, and in vitro cytokine release test.

20 Claims, 6 Drawing Sheets

Zein scores

(51) Int. Cl.
*C11D 1/72* (2006.01)
*C11D 1/90* (2006.01)

(56) References Cited

U.S. PATENT DOCUMENTS

| | | | |
|---|---|---|---|
| 6,024,943 A | 2/2000 | Ness et al. | |
| 6,194,375 B1 | 2/2001 | Ness et al. | |
| 6,242,412 B1 | 6/2001 | Chambers et al. | |
| 6,764,992 B2 | 7/2004 | Kumar et al. | |
| 7,077,870 B2 | 7/2006 | Findlay et al. | |
| 8,426,353 B2 | 4/2013 | Ouali et al. | |
| 2002/0168327 A1* | 11/2002 | Bailey | A61K 8/365 424/70.1 |
| 2003/0215417 A1* | 11/2003 | Uchiyama | A61L 9/01 424/76.2 |
| 2011/0028373 A1* | 2/2011 | Fossum | C11D 3/0052 510/236 |
| 2012/0040003 A1 | 2/2012 | Yarovoy et al. | |
| 2012/0094890 A1 | 4/2012 | Anantaneni et al. | |
| 2013/0072410 A1* | 3/2013 | Germain | A61Q 19/10 510/125 |
| 2013/0326823 A1 | 12/2013 | Somerville Roberts et al. | |
| 2013/0327364 A1 | 12/2013 | Delbrassinne et al. | |
| 2014/0023609 A1 | 1/2014 | Mukherjee et al. | |
| 2014/0352076 A1 | 12/2014 | Song et al. | |
| 2017/0044471 A1* | 2/2017 | Coope-Epstein | C11D 11/0017 |

FOREIGN PATENT DOCUMENTS

| | | |
|---|---|---|
| WO | 1995/032997 A1 | 12/1995 |
| WO | 1997/026315 A1 | 7/1997 |
| WO | 2005070388 A1 | 8/2005 |
| WO | 2010/069957 A1 | 6/2010 |

OTHER PUBLICATIONS

PCT International Search Report & Written Opinion PCT/US2017/042626 Completed: Oct. 27, 2017; dated Oct. 27, 2017 11 pages.

* cited by examiner

Figure 1. Zein scores
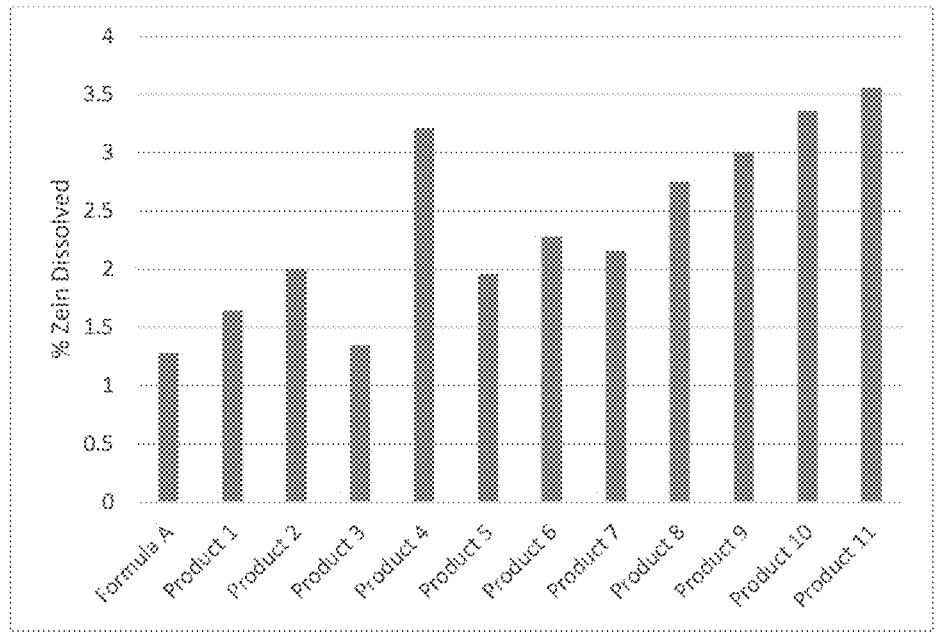
Figure 2. Corneosurfametry Scores
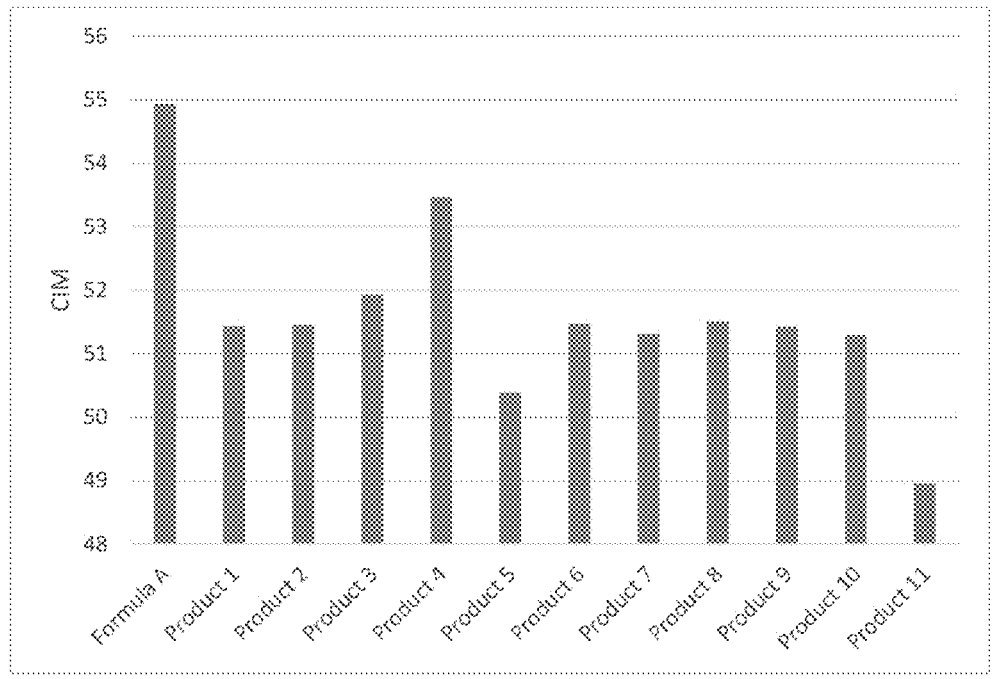

Figure 3. Corneosurfametry Repeat
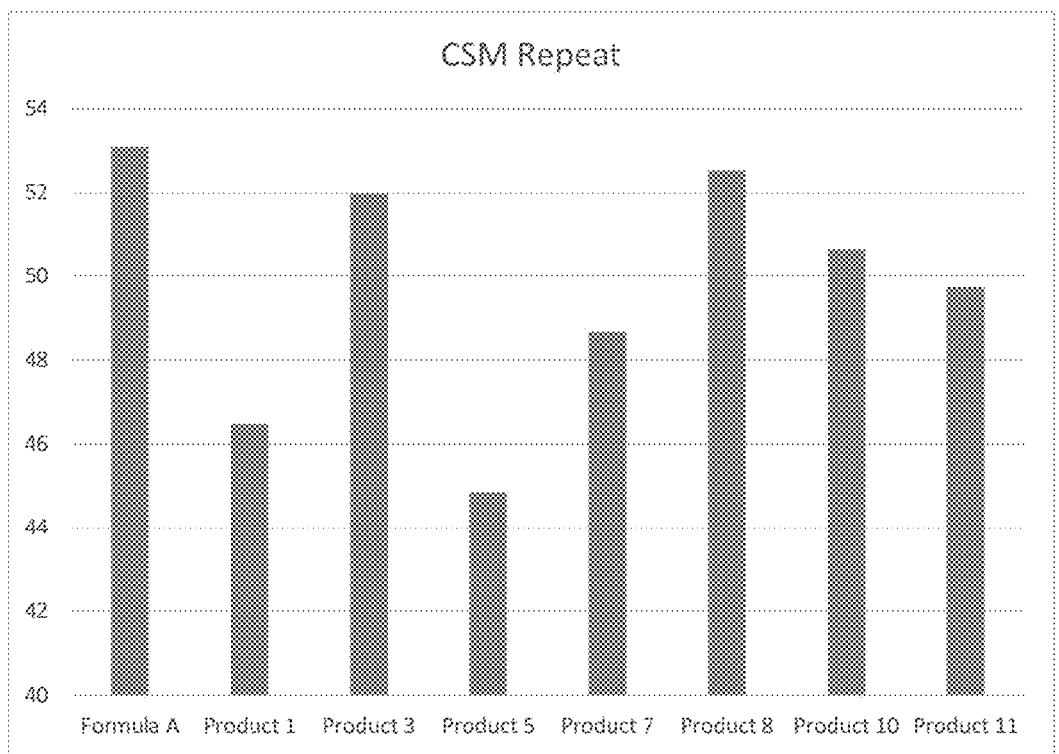

Figure 4. Cytokine 1L-1α
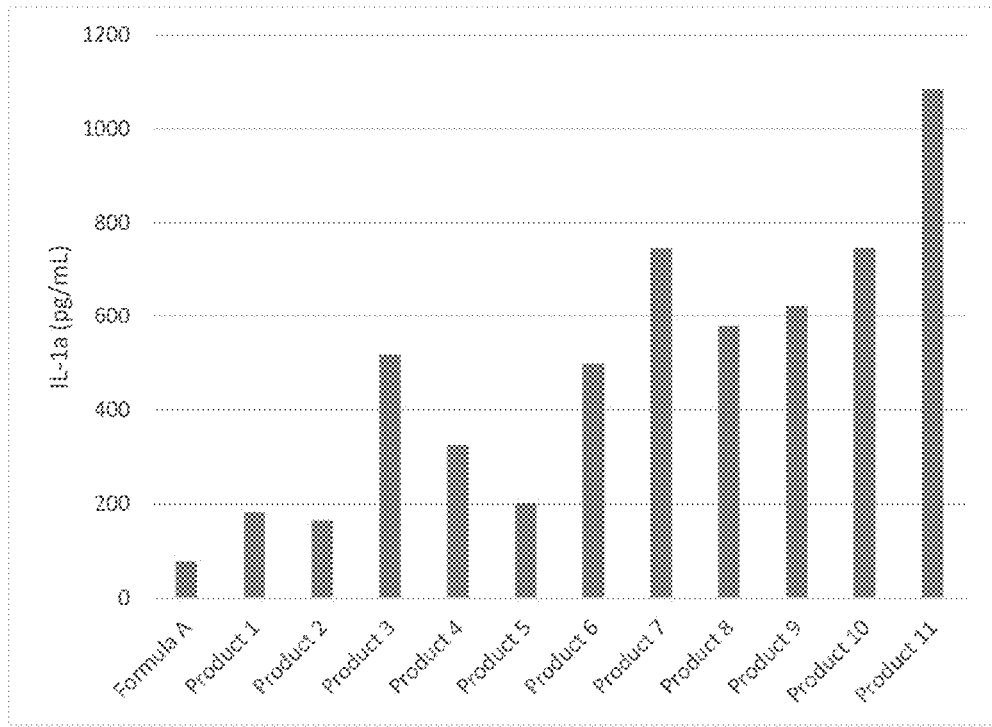
Figure 5. Cytokine 1L-1ra
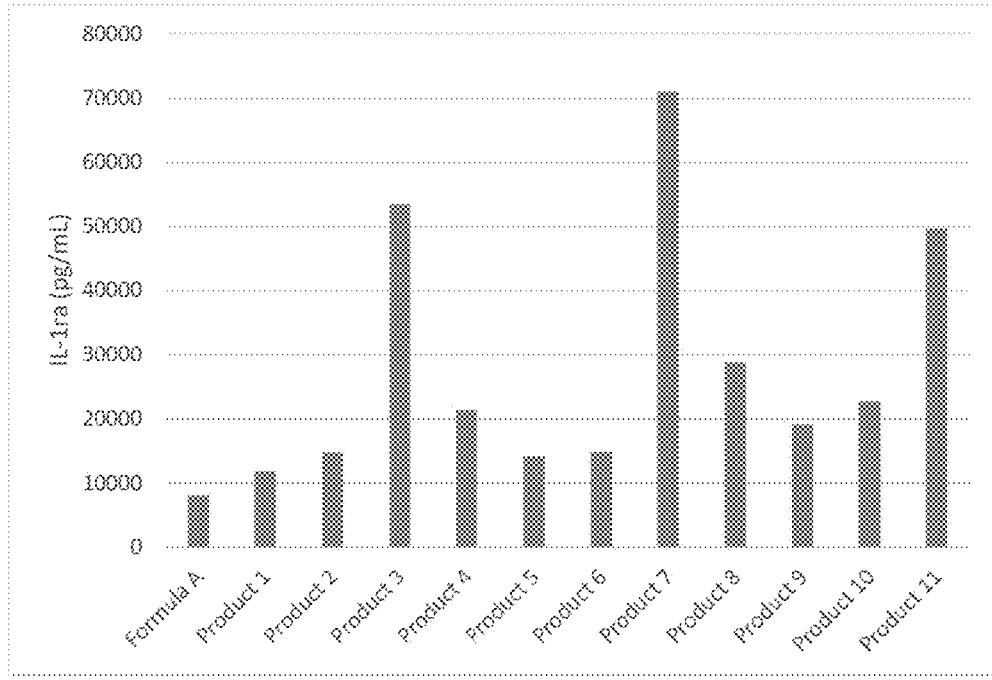

Figure 6. Mildness Indicator
Zein + IL-1α + CSM L*-C*
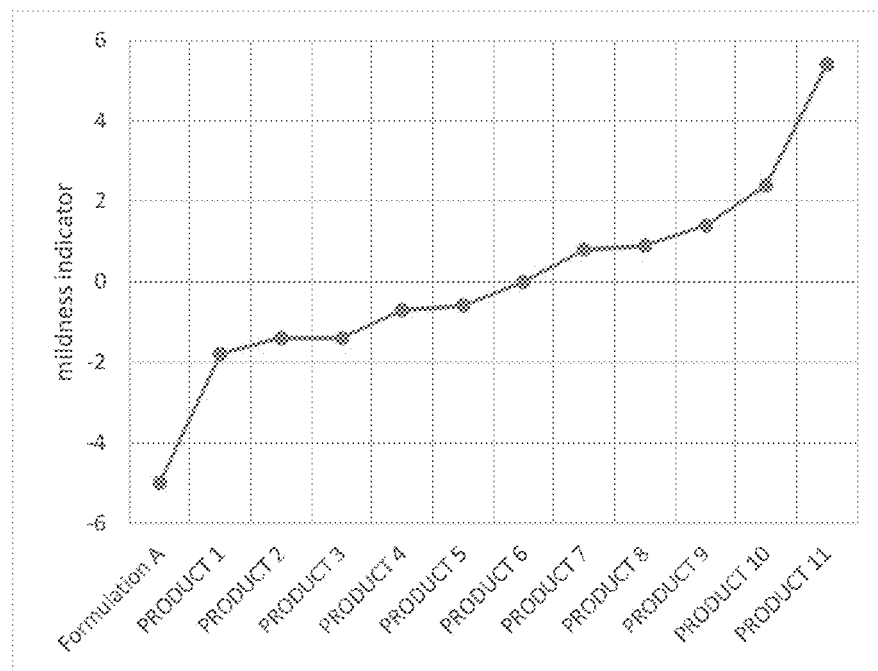

Figure 7. Mildness Indicator
Zein + (IL-1α + IL-1ra) + CSM L*-C*
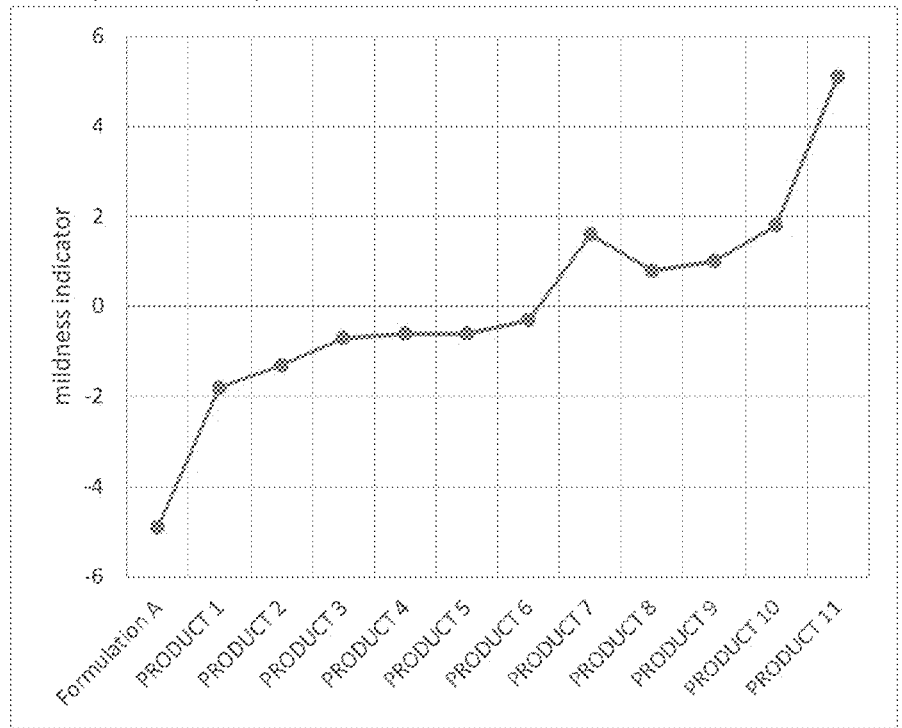
Figure 8. Mildness Indicator
Zein + (IL-1ra/IL-1α) + CSM L*-C*
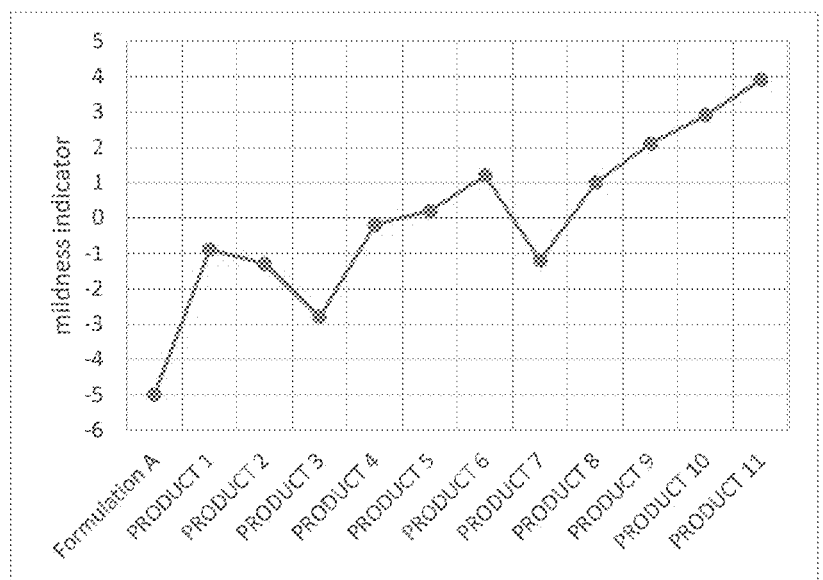

Figure 9. Mildness Indicator
Zein + Log(IL-1ra/IL-1α) + CSM L*-C*
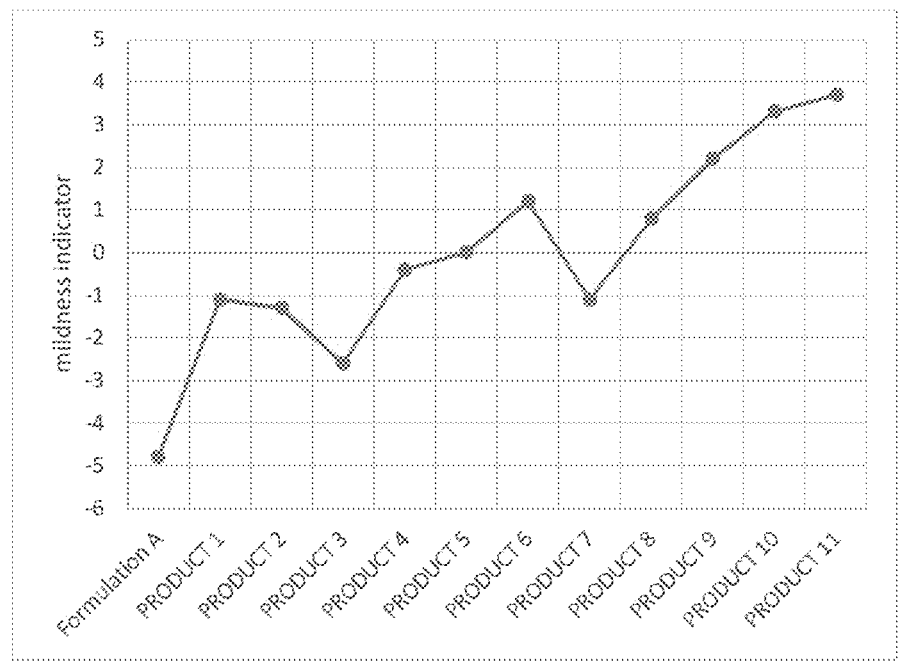
Figure 10. Mildness Indicator
Zein + (IL-1α/IL-1ra) + CSM L*-C*
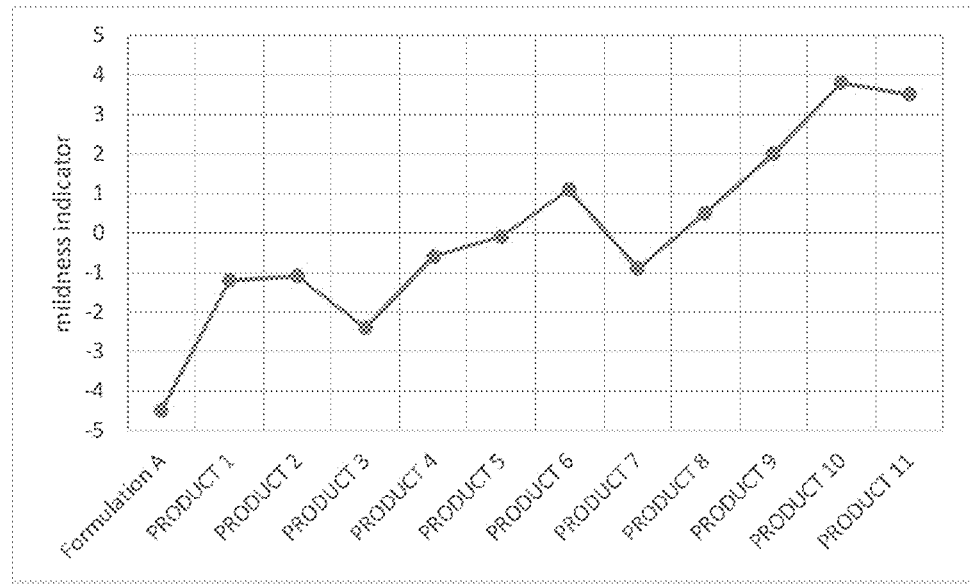

MILD LIQUID DETERGENT FORMULATIONS

FIELD OF INVENTION

The present disclosure is directed to methods for determining mild aqueous laundry detergent formulations, mild liquid laundry detergent formulations, and methods for preparing the same. The formulations comprise various surfactants and have a lower detergent mildness indicator as compared to marketed products.

BACKGROUND

Liquid laundry detergent compositions contain surfactants to have good cleaning performance. However, many surfactant compositions cause skin and eye irritation. There are several methods to measure the skin irritancy potential of a surfactant composition.

One method to test the skin irritancy potential of a surfactant composition is Zein test. Zein score is measured using a Zein test (Gott, E., Aesthet. Medzin., Tenside 15: 313 (1966)). Zein test determines the extent of denaturation of Zein corn protein after exposure to a surfactant for a given period of time. Generally, the higher the Zein score, the greater the skin irritation potential.

Another method to measure the skin irritancy potential is corneosurfametry (CSM) test, a noninvasive quantitative test that measures the interaction between surfactants and human stratum corneum. (Pierard et al., $Dermatology$ 189: 152-156 (1994)). Corneosurfametry involves removing a few layers of skin using cyanoacrylate skin surface strippings, short contact time with surfactants followed by staining the samples with fuchian dyes. A less damaged barrier allows greater penetration of the stain, therefore giving a more intense color, which is measured using colorimetrically with L*a*b* color space. This method is predictive of both protein and lipid damage in the skin. CIM (Color Indicator of Mildness) values are obtained from a corneosurfametry test. In a comparative study, the higher the CIM value, the milder the surfactant formulation.

A third method to evaluate the irritation effect of a surfactant formulation is measured by cytokine release of representative human skin model in response to the surfactant formulation. Where skin tissue viability is not decreased by 50% as compared to the negative control tissue (as measured by MTT reduction), the inflammatory potential is then measured by the production of the cytokines IL-1α and/or IL-1ra. MTT is a dye used to stain the skin cells called 3-(4,5-dimethylthiazol-2-yl)-2,5-diphenyltetrazolium bromide. In a comparative study, a lower cytokine release value means a milder surfactant formulation.

Consumers generally prefer mild liquid detergent formulations, and several products that claim to be mild are currently on the market. There is a still a need to develop improved mild liquid detergent formulations that have good cleaning performance.

SUMMARY

In one aspect, the present invention provides a method for determining a mild aqueous laundry detergent formulation. The method comprises the steps of: (i) providing a solution comprising a laundry cleaning effective amount of a surfactant composition, (ii) subjecting an appropriate dilution of the solution to Zein test, corneosurfametry test, and in vitro cytokine release test for IL-1α and IL-1ra response, respectively, to obtain a Zein score, a corneosurfametric (CSM) value, and a cytokine release value, and (iii) deriving at composite mildness indicator (CMI) for each solution based the Zein score, the CSM value, and the cytokine release value.

The composite mildness indicator (CMI) may also be called detergent mildness indicator (DMI). Specifically, the CMI can be derived from (1) the Zein score, CSM value, and cytokine release value IL-1α of the formulation; (2) the Zein score, CSM value, and cytokine release value (IL-1α+IL-1ra) of the formulation; (3) the Zein score, CSM value, and cytokine release value (IL-1ra/IL-1α) of the formulation; (4) the Zein score, CSM value, and cytokine release value $\log_{10}$(IL-1ra/IL-1α) of the formulation; or (5) the Zein score, CSM value, and cytokine release measurement (IL-1α/IL-1ra) of the formulation.

In some embodiments, the Zein test is tested against a 10% dilution of the solutions, the corneosurfametric test is tested against a 10% dilution of the solutions, and the cytokine release test is tested against a 3% dilution of the solutions.

The present disclosure also provides a method of preparing a mild aqueous laundry detergent formulation, comprising (i) providing solutions comprising a laundry cleaning effective amount of a surfactant composition, (ii) subjecting appropriately diluted solutions to Zein test, corneosurfametry test, and in vitro cytokine release test for IL-1α and IL-1ra response, (iii) obtaining a composite mildness indicator for each solution, (iv) identifying a solution having a composite mildness indicator of less than −3, preferably less than −3.5, more preferably less than −4, or a few units lower than the composite mildness indicator of a reference composition, and (v) adding suitable laundry detergent ingredients to the identified solution.

In some embodiments, the method further comprises a step of adjusting components of the surfactant composition of the solution to adjust its mildness so as to prepare a solution with a desired mildness.

In a further aspect, the present disclosure provides a mild yet effective aqueous laundry detergent formulation comprising a laundry cleaning effective amount of a surfactant composition, and having a composite mildness indicator of at least 3.3 units less than that of a reference detergent composition comprising 20 wt % reference surfactants based on a total weight of the reference detergent composition. The reference surfactants of the said reference detergent composition consist of an alcohol ethoxysulfate (lauryl ethoxyl sulfate, 3EO (AES)) in an amount of 37.5 wt % based on a total weight of the surfactants, a linear alkylbenzenesulfonate (LAS) in an amount of 25 wt % based on a total weight of the surfactants, and a nonionic surfactant alcohol ethoxylate, 7 mole EO in an amount of 37.5 wt % based on a total weight of the surfactants.

In some embodiments, the formulation has one or more of the following characteristics:

(i) the formulation has a Zein score of less than about 3 percent when tested as a 10% dilution, (ii) the formulation has a corneosurfametric color indicator of mildness (CIM) value of greater than about 50 when tested as a 10% dilution, and (iii) the formulation has a cytokine release value of less than about 140 pg/mL IL-1α when tested as a 3% dilution in in vitro cytokine release test.

In some embodiments, the formulation has a Zein score of less than about 3 percent when tested as a 10% dilution.

The present disclosure also provides a mild aqueous laundry detergent formulation comprising a laundry cleaning effective amount of a surfactant composition, wherein the formulation has the following characteristics:

(i) the formulation has a Zein score of less than about 3 percent when tested as a 10% dilution, (ii) the formulation has a corneosurfametric index of mildness (CIM) value of greater than about 50 when tested as a 10% dilution, and (iii) the formulation has a cytokine release value of less than about 140 pg/mL IL-1α when tested as a 3% dilution in in vitro cytokine release test.

In some embodiments, the formulations disclosed herein comprises a surfactant composition comprising a nonionic surfactant, anionic surfactant, and optionally anionic surfactant. In preferred embodiments, a preferred anionic surfactant is alcohol ethoxysulfate (AES); and a preferred anionic surfactant is a linear alkylbenzenesulfonate (LAS).

In some embodiments, the nonionic surfactant is an alcohol ethoxylate (AE).

In some embodiments, the surfactant composition comprises a co-surfactant selected from the group consisting of a zwitterionic surfactant, a high ethoxylation nonionic surfactant, an alkyl polyglucoside (APG), and any combination thereof.

In some embodiments, the nonionic surfactant is present in an amount of from about 30% to about 80% by weight of the surfactant composition, preferably from about 50% to about 70% by weight of the surfactant composition.

In some embodiments, the alcohol ethoxysulfate (AES) in an amount of from about 20% to about 60% by weight of the surfactant composition, preferably from about 30% to about 50% by weight of the surfactant composition.

In some embodiments, the linear alkylbenzenesulfonate (LAS) is present in an amount of from about 0% to about 25% by weight of the surfactant composition.

In some embodiments, the co-surfactant is present in an amount of from about 0.01% to 25% by weight of the surfactant composition.

In some embodiments, the surfactant composition comprises from about 5% to about 60% by weight of the formulation, preferably from about 10% to about 35% by weight of the formulation, more preferably from about 15% to about 25% by weight of the formulation.

In some embodiments, the formulation disclosed herein further comprises a builder component selected from the group consisting of an organic acid, an alkali metal hydroxide, an alkali metal carbonate, an alkali metal bicarbonate, an amine, and mixtures thereof.

In some embodiments, the builder component is selected from the group consisting of citric acid, sodium carbonate, sodium bicarbonate, sodium hydroxide, calcium chloride, triethanolamine, monoethanolamine, and mixtures thereof, in an amount from about 1 wt % to about 8 wt %.

In some embodiments, the formulation disclosed herein further comprises a chelator. In some embodiments, the chelator is a polycarboxylic acid. In some embodiments, the polycarboxylic acid is ethylenediaminetetraacetic acid, succinic acid, iminodisuccinic acid, salts thereof, or mixtures thereof.

In some embodiments, the formulation disclosed herein further comprises at least one additional component selected from the group consisting of a defoamer, an enzyme, a color component, a fragrance component, and mixtures thereof.

In some embodiments, the formulation disclosed herein further comprises a fragrance component. In some embodiments, the fragrance component is encapsulated.

Additional embodiments and advantages of the formulations disclosed herein can be set forth in the detailed description that follows.

It can be to be understood that both the foregoing summary and the following detailed description can be exemplary and explanatory only and can be not restrictive.

BRIEF DESCRIPTION OF THE DRAWINGS

The foregoing summary, as well as the following detailed description of the embodiments, will be better understood when read in conjunction with the appended figures. For the purpose of illustration, the figures may describe the use of specific embodiments. It should be understood, however, that the formulations described herein cannot be limited to the precise embodiments discussed or described in the figures.

FIG. 1 depicts the results of Zein test for Formulation A and commercial Products 1-11.

FIG. 2 depicts the results of corneosurfametry test for Formulation A and commercial Products 1-11.

FIG. 3 depicts the results of a second corneosurfametry test for Formulation A and commercial Products 1, 3, 5, 7, 8, 10 and 11.

FIG. 4 depicts the results of cytokine release test for Formulation A and commercial Products 1-11 on IL-1α.

FIG. 5 depicts the results of cytokine release test for Formulation A and commercial Products 1-11 on IL-1ra.

FIG. 6 depicts comparison of Formulation A and commercial Products 1-11 on composite mildness indicators derived from Zein score, CSM value, and cytokine value (IL-1α).

FIG. 7 depicts comparison of Formulation A and commercial Products 1-11 on composite mildness indicators derived from Zein score, CSM value, and cytokine value (IL-1α+IL-1ra).

FIG. 8 depicts comparison of Formulation A and commercial Products 1-11 on composite mildness indicators derived from Zein score, CSM value, and cytokine value (IL-1ra/IL-1α).

FIG. 9 depicts comparison of Formulation A and commercial Products 1-11 on composite mildness indicators derived from Zein score, CSM value, and cytokine value ($\log_{10}$(IL-1ra/IL-1α)).

FIG. 10 depicts comparison of Formulation A and commercial Products 1-11 on composite mildness indicators derived from Zein score, CSM value, and cytokine value) (IL-1α/IL-1ra).

DETAILED DESCRIPTION

The articles "a," "an," and "the" can be used herein to refer to one or to more than one (i.e., to at least one) of the grammatical object of the article, unless the language and/or context clearly indicates otherwise. By way of example, "an element" means one element or more than one element.

As used herein, the terms "comprises," "comprising," "having," "including," "containing," and the like can be open-ended terms meaning "including, but not limited to."

As used herein, the term "about" means±10% of the recited value. Thus, and by way of example only, the phrase "about ten" means 9 to 11.

As used herein, "percent" and "%" refer to weight percentage unless otherwise specified. As used herein, the phrase "substantially free" or "substantially X-free," wherein X is a specified ingredient, means that a given formulation is at least about 97 percent by weight free of the specified ingredient, and in certain embodiments as specified herein, at least about 98, at least about 99, at least about 99.9, or at least about 99.99 percent by weight free of the specified ingredient.

As used herein, the phrase "weight percent," "percent by weight," and the like mean weight percent based on the quantity of active agent in a given component. For example, certain components of the formulations disclosed herein are only commercially available as X weight percent solutions in water. A formulation described herein including Y weight percent of the component that is an X weight percent aqueous solution is calculated based on the amount of active ingredient in the aqueous solution and not the weight of the total aqueous solution added to the formulation. That is, and by way of example only, a formulation weighing 100 g and including 10 weight percent of component A (the "active"), which is only commercially available as a 50 weight percent (w/w, or wt %) aqueous solution, includes 10 g of component A—even though 20 g of the commercial solution was added to the formulation to reach 10 weight percent. For a pure solid, weight percent is calculated using standard techniques.

As used herein, the term "dilution" means that a formulation is diluted with water to make a diluted product. For example, "10% dilution" means a diluted product containing 10 wt % of the original formulation.

As used herein, the term weight fraction refers to the fraction of the total component wherein the total component equals 1.0. So, for example, a weight fraction of surfactant X of 0.50 means that 0.50/1.0=50% of the total surfactant is component X. In other words, surfactant X is present in an amount of 50% of the total surfactant.

The present disclosure provides a mild aqueous laundry detergent formulation, comprising a laundry cleaning effective amount of a surfactant composition, and having a composite mildness indicator of less than −3, preferably less than −3.5, more preferably less than −4, or a few units lower than the composite mildness indicator of a reference composition. In some embodiments, the formulation has a composite mildness indicator of less than −5 or less than −4.5. In some embodiments, the formulation has a composite mildness indicator of from about −5 to about −2, from about −4.5 to about −2, from about −4 to about −2, from about −3.5 to about −2, from about −3 to about −2, or from about −2.5 to about −2. In some embodiments, the formulation has a composite mildness indicator of from about −5 to about −2.5, from about −5 to about −3, from about −5 to about −3.5, from about −5 to about −4, or from about −5 to about −4.5.

In some embodiments, such mild aqueous laundry detergent formulations have one or more of the following characteristics:

(i) the formulation has a Zein score of less than about 3 percent when tested as a 10% dilution, (ii) the formulation has a corneosurfametric index of mildness (CIM) value of greater than about 50 when tested as a 10% dilution, and (iii) the formulation has a cytokine release value of less than about 140 pg/mL when tested as a 3% dilution in in vitro cytokine release test for IL-1α response.

The present disclosure also provides a mild aqueous laundry detergent formulation comprising a laundry cleaning effective amount of a surfactant composition, wherein the formulation has the following characteristics:

(i) the formulation has a Zein score of less than about 3 percent when tested as a 10% dilution, (ii) the formulation has a corneosurfametric (CSM) value of greater than about 50 when tested as a 10% dilution, and (iii) the formulation has a cytokine release value of less than about 140 pg/mL IL-1α when tested as a 3% dilution in in vitro cytokine release test.

As used herein the phrase "Zein score" refers the measurement obtained from the Zein test as described in the Examples. It can also be referred to as "Zein solubilized %."

In some embodiments, the formulations described herein have a Zein score of less than about 3% when tested as a 10% dilution. In certain embodiments, the formulations have a Zein score of from about 0.01% to about 3%, from about 0.01% to about 2.75%, from about 0.01% to about 2.5%, from about 0.01% to about 2.25%, from about 0.01% to about 2%, from about 0.01% to about 1.75%, from about 0.01% to about 1.5%, from about 0.01% to about 1.25%, or from about 0.01% to about 1% when tested as a 310% dilution. In other embodiments, the formulations described herein can have a Zein score of less than about 2.75%, less than about 2.5%, less than about 2.25%, less than about 2%, less than, 1.75%, less than about 1.5%, less than about 1.25%, or less than about 1% when tested as a 10% dilution.

As used herein the phrase "Color Indicator of Mildness (CIM)" refers to the measurement obtained from corneosurfametry (CSM) test as described in the Examples. It can also be referred to as "CSM L*-C*."

In some embodiments, the formulations described herein have a CIM value of greater than about 50 when tested as a 10% dilution. In certain embodiments, the formulations have a CIM value of from about 60 to about 74, from about 60 to about 73, from about 60 to about 72, from about 60 to about 71, from about 60 to about 70, from about 60 to about 69, from about 60 to about 68, from about 60 to about 67, from about 60 to about 66, or from about 60 to about 65 when tested as a 3% active surfactant solution. In other embodiments, the formulations have a CIM value of from about 55 to about 74, from about 55 to about 70, from about 55 to about 65, or from about 55 to about 60 when tested as a 10% dilution. In other embodiments, the formulations have a CIM value of from about 50 to about 74, from about 50 to about 70, from about 50 to about 65, from about 50 to about 60, or from about 50 to about 55 when tested as a 10% dilution.

As used herein the phrases "cytokine release value" and "cytokine value" are interchangeable and refer to the measurement obtained in in vitro cytokine release test for IL-1α or IL-1ra release as described in the Examples.

In some embodiments, the formulations described herein have a cytokine release value of less than about 140 pg/mL IL-1α when tested as a 3% dilution in in vitro cytokine release test. In certain embodiments, the formulations have a cytokine release value (IL-1α) of less than about 200, less than about 150 pg/mL, or less than about 100 pg/mL when tested as a 3% dilution in in vitro cytokine release test. In certain embodiments, the formulations have a cytokine release value (IL-1α) of from about 40 to about 90 pg/mL, from about 40 to about 85 pg/mL, from about 40 to about 80 pg/mL, from about 40 to about 75 pg/mL, from about 40 to about 70 pg/mL, from about 40 to about 65 pg/mL, from about 40 to about 60 pg/mL, from about 40 to about 55 pg/mL, from about 40 to about 50 pg/mL, or from about 40 to about 45 pg/mL when tested as a 3% dilution in in vitro cytokine release test. In other embodiments, the formulations have a cytokine release value (IL-1α) of from about 45 to about 90 pg/mL, from about 50 to about 90 pg/mL, from about 55 to about 90 pg/mL, from about 60 to about 90 pg/mL, from about 65 to about 90 pg/mL, from about 70 to about 90 pg/mL, from about 75 to about 90 pg/mL, from about 80 to about 90 pg/mL, or from about 85 to about 90 pg/mL when tested as a 3% dilution in in vitro cytokine release test. In other embodiments, the formulations have a cytokine release value (IL-1α) of from about 45 to about 140 pg/mL, from about 50 to about 140 pg/mL, from about 55 to about 140 pg/mL, from about 60 to about 140 pg/mL, from about 65 to about 140 pg/mL, from about 70 to about 140 pg/mL, from about 75 to about 140 pg/mL, from about 80 to about 140 pg/mL, from about 85 to about 140 pg/mL, from about 90 to about 140 pg/mL, from about 100 to about 140 pg/mL, from about 110 to about 140 pg/mL, from about 120 to about 140 pg/mL, or from about 130 to about 140 pg/mL when tested as a 3% dilution in in vitro cytokine release test.

The formulations of the present disclosure can have a Zein score disclosed herein, a CIM value disclosed herein, and a cytokine release value (IL-1α) disclosed herein.

The present disclosure provides mild aqueous laundry detergent formulations, comprising a cleaning effective amount of a surfactant composition, wherein the formulation has a composite mildness indicator of less than −3, preferably less than −3.5, more preferably less than −4, or a few units lower than the composite mildness indicator of a reference composition.

As used herein, the phrase "laundry cleaning effective amount" refers to any amount capable of producing a cleaning, stain removal, and/or soil removal effect on the treated substrate. A person of ordinary skill in the art would understand how to determine a laundry cleaning effective amount for the mild aqueous laundry detergent formulations disclosed herein.

As used herein, the phrase "composite mildness indicator" ("CMI") refers to a mildness index calculated as the sum of the standardized Zein and CSM values plus one of the standardized cytokine values (IL-1α, Total Cytokine, IL-1ra/IL-1α, IL-1α/IL-1ra, or $\log_{10}$(IL-1ra/IL-1α)), as described in the Examples. Composite mildness indicators can be used to evaluate mildness of multiple detergent formulations/products.

The phrase "detergent mildness indicator" ("DMI") is used interchangeably with the term "composite mildness indicator" ("CMI").

As used herein, the phrase "Partial-DMI" refers to a mildness index calculated as the sum of the standardized Zein test and total cytokine values. CSM values are not part of the calculation.

In some embodiments, the formulations disclosed herein comprises a surfactant composition comprising a nonionic surfactant, alcohol ethoxysulfate (AES), and optionally a linear alkylbenzenesulfonate (LAS). In some embodiments, the surfactant composition further comprises a co-surfactant selected from the group consisting of a zwitterionic surfactant, a high ethoxylation nonionic surfactant, an alkyl polyglucoside (APG), and any combination thereof.

In some embodiments, the surfactant composition comprises from about 5% to about 60% by weight of the formulation. In some embodiments, the surfactant composition comprises from about 5% to about 55%, from about 5% to about 50%, from about 5% to about 45%, from about 5% to about 40%, from about 5% to about 35%, from about 5% to about 30%, from about 5% to about 25%, from about 5% to about 20%, from about 5% to about 15%, or from about 5% to about 10% by weight of the formulation. In some embodiments, the surfactant composition comprises from about 10% to about 30%, from about 10% to about 25%, from about 10% to about 20%, from about 10% to about 15%, from about 15% to about 30%, from about 15% to about 25%, from about 15% to about 20%, from about 20% to about 30%, from about 20% to about 25%, or from about 25% to about 30% by weight of the formulation. In some embodiments, the surfactant composition comprises about 5%, about 10%, about 15%, about 20%, about 25%, or about 30% by weight of the formulation. In some embodiments, the surfactant composition comprises about 18% by weight of the formulation.

Nonionic Surfactant

In some embodiments, the nonionic surfactant is an alcohol ethoxylate (AE). In some embodiments, the nonionic surfactant can be an aliphatic primary alcohol ethoxylate. In some embodiments, the ethoxylated nonionic surfactant can be an aliphatic secondary alcohol ethoxylate. In some embodiments, the alcohol ethoxylates can be the condensation products of an organic aliphatic or alkyl aromatic hydrophobic compound and hydrophilic ethylene oxide groups. The length of the polymerized ethylene oxide chain can be adjusted to achieve the desired balance between the hydrophobic and hydrophilic elements.

In some embodiments, the nonionic surfactant includes the condensation products of a higher alcohol (e.g., an alkanol containing 8 to 16 carbon atoms in a straight or branched chain configuration) condensed with 4 to 20 moles of ethylene oxide, for example, lauryl or myristyl alcohol condensed with 16 moles of ethylene oxide (EO), tridecanol condensed with 6 moles of EO, myristyl alcohol condensed with 10 moles of EO per mole of myristyl alcohol, the condensation product of EO with a coconut fatty alcohol containing a mixture of fatty alcohols with alkyl chains varying from 10 to 14 carbon atoms in length and wherein the condensate contains either 6 moles of EO per mole of total alcohol or 9 moles of EO per mole of alcohol, and tallow alcohol ethoxylates containing 6 EO to 11 EO per mole of alcohol.

In some embodiments, the nonionic surfactant can be a higher aliphatic, primary alcohol containing 9-15 carbon atoms, such as $C_9$-$C_{11}$ alkanol condensed with 4 to 10 moles of ethylene oxide, $C_{12}$-$C_{13}$ alkanol condensed with 6.5 moles ethylene oxide (for example, NEODOL 91-8 or NEODOL 9-15 (Shell Chemicals, Netherlands)), $C_{12}$-$C_{15}$ alkanol condensed with 12 moles ethylene oxide (for example, NEODOL 25-12 (Shell Chemicals, Netherlands)), $C_{12}$-$C_{15}$ alkanol condensed with 9 moles ethylene oxide (for example, NEODOL 25-9 (Shell Chemicals, Netherlands)), $C_{14}$-$C_{15}$ alkanol condensed with 13 moles ethylene oxide (for example, NEODOL 45-13 (Shell Chemicals, Netherlands)), or a $C_{12}$-$C_{15}$ alkanol condensed with 2, 3, 4, 7, 9, or 10 moles of ethylene oxide.

In some embodiments, the nonionic surfactant can be a $C_{12}$-$C_{15}$ alkanol condensed with 7 moles of ethylene oxide. In some embodiments, the $C_{12}$-$C_{14}$ alkanol condensed with 7 moles of ethylene oxide can be NEODOL 25-7 (Shell Chemicals, Netherlands).

Additional satisfactory alcohol ethylene oxide condensates can be the condensation products of a secondary aliphatic alcohol containing 8 to 18 carbon atoms in a straight or branched chain configuration condensed with 5 to 30 moles of ethylene oxide. Examples of commercially available nonionic surfactants of the foregoing type can be $C_{12}$-$C_{14}$ secondary alkanol condensed with either 9 EO (TERGITOL™ 15-S-9 (Dow Chemical Company, Michigan, United States)) or 12 EO (TERGITOL™ 15-S-12 (Dow Chemical Company, Michigan, United States)).

In still other embodiments, the nonionic surfactant can be a methyl ester ethoxylate having the formula $RC(=O)(OCH_2CH_2)_xOCH_3$ where R is an alkyl chain having from 12 to 18 carbon atoms and x is 6, 7, 8, 9, 10, 11, 12, 13, 14, or 15. In certain embodiments, R is an alkyl chain having from 12 to 14 carbon atoms and x is 15. In still other embodiments, R is an alkyl chain having 18 carbon atoms and x is 15. These surfactants are available from Lion Corporation.

In some embodiments, the nonionic surfactant is present in an amount of from about 25% to about 75% by weight of the surfactant composition. In some embodiments, the nonionic surfactant is present in an amount of from about 30% to about 70%, from about 35% to about 70%, from about 40% to about 70%, from about 45% to about 70%, from about 50% to about 70%, from about 55% to about 70%, from about 60% to about 70%, or from about 65% to about 70% by weight of the surfactant composition. In some embodiments, the nonionic surfactant is present in an amount of from about 30% to about 65%, from about 30% to about 60%, from about 30% to about 55%, from about 30% to about 50%, from about 30% to about 45%, from about 30% to about 40%, or from about 30% to about 35% by weight of the surfactant composition. In some embodiments, the nonionic surfactant is present in an amount of about 30%, about 35%, about 40%, about 45%, about 50%, about 55%, about 60%, about 65%, or about 70% by weight of the surfactant composition. In other embodiments, the nonionic surfactant is present in an amount of from about 25% to about 90% by weight of the surfactant composition.

Alcohol Ethoxysulfate (AES)

Alcohol ethoxysulfate (AES), also known as alkyl ether sulfates or alkyl polyethoxylate sulfates, are those which correspond to the following formula (I):

$$R'-O-(C_2H_4O)_n-SO_3M' \quad (I)$$

wherein R' is a $C_8$-$C_{20}$ alkyl group, n is from 1 to 20, and M' is a salt-forming cation; preferably, R' is $C_{10}$-$C_{18}$ alkyl, n is from 1 to 15, and M' is sodium, potassium, ammonium, alkylammonium, or alkanolammonium. In another embodiment, R' is a $C_{12}$-$C_{16}$ alkyl, n is from 1 to 6 and M' is sodium. In another embodiment, the alkyl ether sulfate is sodium lauryl ether sulfate (SLES).

The alcohol ethoxysulfate is generally used in the form of mixtures comprising varying R' chain lengths and varying degrees of ethoxylation. Frequently such mixtures inevitably also contain some unethoxylated alkyl sulfate materials, i.e., surfactants of the above ethoxylated alkyl sulfate formula wherein n=0. Unethoxylated alkyl sulfates may also be added separately to the liquid compositions of this invention. Suitable unalkoxylated, e.g., unethoxylated, alkyl ether sulfate surfactants are those produced by the sulfation of higher $C_8$-$C_{20}$ fatty alcohols. Conventional primary alkyl sulfate surfactants have the general formula of: $ROSO_3M$, wherein R is typically a linear $C_8$-$C_{20}$ hydrocarbyl group, which may be a straight chain or branched chain, and M is a water-solubilizing cation; preferably R is a $C_{10}$-$C_{15}$ alkyl, and M is alkali metal. In one embodiment, R is $C_{12}$-$C_{14}$ and M is sodium.

In some embodiments, the alcohol ethoxysulfate is present in an amount of from about 20% to about 60% by weight of the surfactant composition. In some embodiments, the alcohol ethoxysulfate is present in an amount of from about 20% to about 60%, from about 25% to about 60%, from about 30% to about 60%, from about 35% to about 60%, from about 40% to about 60%, from about 45% to about 60%, from about 50% to about 60%, or from about 55% to about 60% by weight of the surfactant composition. In some embodiments, the alcohol ethoxysulfate is present in an amount of from about 20% to about 55%, from about 20% to about 50%, from about 20% to about 45%, from about 20% to about 40%, from about 20% to about 35%, from about 20% to about 30%, or from about 20% to about 25% by weight of the surfactant composition. In some embodiments, the alcohol ethoxysulfate is present in an amount of about 20%, about 25%, about 30%, about 35%, about 40%, about 45%, about 50%, about 55%, or about 60% by weight of the surfactant composition. In other embodiments, the alcohol ethoxysulfate is present in an amount of from about 0%% to about 60% by weight of the surfactant composition.

Alkylbenzenesulfonate (LAS)

Alkylbenzenesulfonate (LAS) is a water soluble salt of a linear alkyl benzene sulfonate having between 8 and 22 carbon atoms in the alkyl group. In one embodiment, the LAS comprises an alkali metal salt of $C_{10-16}$ alkyl benzene sulfonic acids, such as $C_{11-14}$ alkyl benzene sulfonic acids. Suitable LAS include sodium and potassium linear, straight chain alkylbenzene sulfonates in which the average number of carbon atoms in the alkyl group is between 11 and 14. Sodium $C_{11}$-$C_{14}$, e.g., $C_{12}$, LAS is one suitable anionic surfactant for use herein.

In some embodiments, the formulation disclosed herein does not comprise a LAS. In some embodiments, the formulation disclosed herein comprises a LAS.

In some embodiments, the LAS is present in an amount of from about 0% to about 30% by weight of the surfactant composition. In some embodiments, the LAS is present in an amount of from about 0.01% to about 25%, from about 0.01% to about 20%, from about 0.01% to about 15%, from about 0.01% to about 10%, from about 0.01% to about 5%, from about 0.01% to about 1%, or from about 0.01% to about 0.5% by weight of the surfactant composition. In some embodiments, the LAS is present in an amount of from about 0.5% to about 25%, from about 1% to about 25%, from about 5% to about 25%, from about 10% to about 25%, from about 15% to about 25%, or from about 20% to about 25% by weight of the surfactant composition. In some embodiments, the LAS is present in an amount of about 0.01%, about 0.5%, about 1%, about 5%, about 10%, about 15%, about 20%, or about 25% by weight of the surfactant composition.

Co-Surfactant

In addition to the above described nonionic surfactant, AES, and LAS, the formulations of the present disclosure can comprise an additional surfactant—a co-surfactant. In some embodiments, the formulations of the present disclosure can comprise a co-surfactant selected from the group consisting of a zwitterionic surfactant, a high ethoxylation nonionic surfactant, an alkyl polyglucoside (APG), and any combination thereof.

Zwitterionic surfactants, also known as amphoteric surfactants, have both cationic and anionic centers attached to the same molecule. In certain embodiments, the zwitterionic surfactant can be a betaine having the general structure:

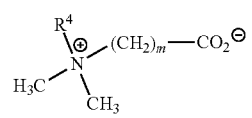

wherein $R^4$ is a hydrocarbon chain containing from 8 to 18 carbon atoms, interrupted by an amide group, and m is an integer from 1 to 4. In certain embodiments, $R^4$ is $R^5$—CONH—$(CH_2)_n$— wherein $R^5$ is a linear or branched $C_8$-$C_{18}$ alkyl group and n is 2, 3, or 4. In some embodiments, $R^5$ is a linear $C_8$-$C_{18}$ alkyl group and n is 2, 3, or 4. In some embodiments, $R^5$ is a linear $C_{11}$ alkyl group and n is 3 (cocoamidopropyl betaine ("CAPB")).

A high ethoxylation nonionic surfactant is a nonionic surfactant having a high degree of ethoxylation. Such high ethoxylation nonionic surfactants can include a moiety of $(C_2H_4O)_n$ where n is at least 8, at least 10, at least 12, at least 14, at least 16, at least 18, or at least 20.

In certain embodiments, the formulations of the present disclosure can comprise an alkyl polyglucoside ("APG"), or a mixture of alkyl polyglucosides, each having the formula:

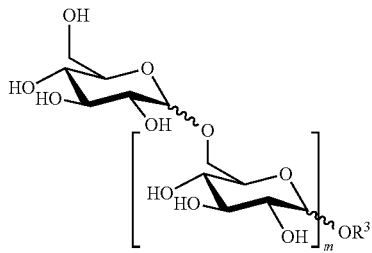

wherein m is an integer from 1 to 10 and $R^3$ is a linear or branched $C_8$-$C_{18}$ alkyl group. Alkyl polyglucosides and methods for preparing them are well known in the art and are discussed, generally, in WO 1997/026315, U.S. Pat. No. 7,077,870, U.S. Pat. No. 3,598,865, U.S. Pat. No. 4,565,647, EP 132043, and EP 132046, each of which is incorporated by reference in its entirety.

In particular embodiments, the alkyl polylglucoside can be an aqueous mixture of alkyl polyglucosides, such as a GLUCOPON, specific examples of which include GLUCOPON 420 UP (CAS 110615-47-9 and 68515-73-1), GLUCOPON 425 N (CAS 110615-47-9 and 68515-73-1) (sold in some markets as GLUCOPON 425 N/HH), GLUCOPON 600 UP (CAS 110615-47-9) (sold in some markets as GLUCOPON 600 CSUP), and GLUCOPON 650 EC (CAS 110615-47-9 and 68515-73-1), all available from BASF.

In some embodiments, the formulation disclosed herein does not comprise a co-surfactant. In some embodiments, the formulation disclosed herein comprises a co-surfactant.

In some embodiments, the co-surfactant is present in an amount of from about 0% to about 25% by weight of the surfactant composition. In some embodiments, the co-surfactant is present in an amount of from about 0.01% to about 25%, from about 0.01% to about 20%, from about 0.01% to about 15%, from about 0.01% to about 10%, from about 0.01% to about 5%, from about 0.01% to about 1%, or from about 0.01% to about 0.5% by weight of the surfactant composition. In some embodiments, the co-surfactant is present in an amount of from about 0.5% to about 25%, from about 1% to about 25%, from about 5% to about 25%, from about 10% to about 25%, from about 15% to about 25%, or from about 20% to about 25% by weight of the surfactant composition. In some embodiments, the co-surfactant is present in an amount of about 0.01%, about 0.5%, about 1%, about 5%, about 10%, about 15%, about 20%, or about 25% by weight of the surfactant composition.

Other Components

In addition to the components noted above, the formulations described herein can also contain one or more ingredients conventionally included in fabric treatment formulations such as pH buffering or adjusting agents, builders, metal chelating agents, enzymes, anti-redeposition polymers, soil-release polymers, perfumes, fluorescent agents, shading dyes, colorants, hydrotropes, antifoaming agents, polyelectrolytes, optical brightening agents, pearlescers, anti-shrinking agents, anti-wrinkle agents, anti-spotting agents, germicides, fungicides, anti-corrosion agents, drape imparting agents, anti-static agents, ironing aids, crystal growth inhibitors, anti-oxidants, and anti-reducing agents. Examples and sources of suitable such components are well-known in the art and/or are described herein.

For example, in some embodiments, the formulation can comprise a polyol, such as glycerin (glycerol) or propylene glycol as a hydrotrope. In some embodiments, the formulation comprises from about 1% to about 25%, from about 1% to about 20%, from about 1% to about 15%, from about 1% to about 10%, from about 1% to about 5%, or from about 1% to about 2.5% glycerin by weight. In some embodiments, the formulation can comprise about 5% or about 2.5% glycerin by weight. In other embodiments, however, the formulation can be completely or substantially glycerin free.

The formulations described herein can further include one or more pH adjusting agents. Suitable pH adjusting agents are known to those of ordinary skill in the art but include acids such as hydrochloric acid and bases such as sodium hydroxide, citric acid, triethanolamine, and monoethanolamine. For example, in certain embodiments, the present formulations can include an appropriate amount of one or more pH adjusting agents such that the pH of the formulation ranges from about 7 to about 8.5. In particular embodiments, the pH can range from about 7 to about 8, from about 7 to about 7.75, from about 7 to about 7.5, or from about 7 to about 7.25. In other embodiments, the pH can be about 7, about 7.25, about 7.5, about 7.75, about 8, about 8.25, or about 8.5. In some other embodiments, the formulation has a pH of from about 8.5 to about 13, from about 8.5 to about 12, from about 8.5 to about 11, from about 8.5 to about 10, or from about 8.5 to about 9. In some embodiments, the pH of the formulation can be about 9, about 9.5, about 10, about 10.5, about 11, about 11.5, about 12, about 12.5, or about 13.

In certain embodiments, the formulations described herein can include more than one pH adjusting agent, with each pH adjusting agent present at from about 0.1% to about 5% by weight. In other embodiments, each pH adjusting agent can be present from about 0.1% to about 4% by weight, from about 0.1% to about 3% by weight, from about 0.1% to about 2% by weight or from about 0.1% to about 1% by weight.

In certain embodiments, the formulation can comprise at least one of citric acid, sodium hydroxide, and triethanolamine. In certain embodiments, the formulation can include citric acid, triethanolamine, and sodium hydroxide.

In certain embodiments, the citric acid can be present at from about 0.5% to about 5% by weight, and in particular embodiments, at about 1% by weight or at about 2% by weight. In some embodiments, the citric acid can be present at about 1.5% by weight. In other embodiments, however, the formulation can be completely or substantially citric acid free.

In certain embodiments, the triethanolamine can be present from about 0.5% by weight to about 2% by weight. In certain embodiments, the triethanolamine can be present from about 0.7% by weight to about 1.5% by weight. And in still further embodiments, the triethanolamine can be present at about 1% by weight. In other embodiments, however, the formulations can be completely or substantially triethanolamine free.

Sodium hydroxide, when present, can be added in an amount sufficient to achieve the desired pH. But in certain embodiments, the amount of sodium hydroxide in the formulation can range from about 0.5% by weight to about 2% by weight. In still other embodiments, the amount of sodium hydroxide can range from about 0.7% by weight to about 1.5% by weight. In still other embodiments, the amount of sodium hydroxide present in the formulation can be about 0.5 to about 0.8% by weight or about 1% by weight to about 2% by weight.

In certain embodiments, the formulation can also comprise a metal chelating agent. Suitable metal chelating agents include polycarboxylic acids such as methyl glycinediacetic acid (MGDA), succinic acid, iminodisuccinic acid (IDS), trisodium ethylenediamine disuccinate (EDDS), pentasodium diethylenetriamine pentatacetate. (DTPA), carboxymethylated polyethyleneimine (trade name Trilon P from BASF), ethylenediaminetetrasaceticacid (EDTA), salts of any of the foregoing, and mixture of any of the foregoing. Other suitable chelating agents include those sold by Dow under the VERSENEX trade name, by BASF under the TRILON trade name, and by Akzo Nobel under the DISSOLVINE trade name.

In certain embodiments, the chelating agent can be present from about 0.01% by weight to about 4.0% by weight. In other embodiments, the chelating agent can be present from about 0.1% to about 2% by weight, or from about 0.2% by weight to about 1% by weight. In other embodiments, the chelating agent can be present at about 0.25% by weight. In one embodiment, the chelating agent can be iminodisuccinic acid.

In certain embodiments, the formulations can also include one or more biocidal agents such as triclosan (5-chloro-2 (2,4-dichloro-phenoxy) phenol), and the like.

In further embodiments, the formulations described herein can also include one or more optical brighteners such as TINOPAL® AMS (a stillbene), TINOPAL 5BM-GX (stilbene disulfonic acid derivative), TINOPAL® CBS-X (a distyrylbiphenyl derivative), and/or a stilbene/naphthotriazole blend such as TINOPAL® RA-16, all sold by BASF. In some embodiments, the optical brightener can be present from about 0.01% to about 0.5% by weight, from about 0.01% to about 0.4% by weight, from about 0.1% to about 0.3% by weight, from about 0.15% to about 0.25% by weight, or about 0.2% or about 0.1% by weight.

The formulations described herein can further include an enzyme. Suitable enzymes include those known in the art, such as amylolytic, proteolytic, cellulolytic, or lipolytic type, and those listed in U.S. Pat. No. 5,958,864, the disclosure of which is incorporated herein by reference in its entirety. One suitable protease, sold under the trade name SAVINASE® by Novo Nordisk Industries A/S, is a subtilase from *Bacillus lentus*. Other suitable enzymes include proteases, amylases, lipases and cellulases, such as ALCALASE® (bacterial protease), EVERLASE® (protein-engineered variant of SAVINASE®), ESPERASE® (bacterial protease), LIPOLASE® (fungal lipase), LIPOLASE ULTRA (protein-engineered variant of LIPOLASE), LIPOPRIME® (protein-engineered variant of LIPOLASE), TERMAMYL® (bacterial amylase), BAN (Bacterial Amylase Novo), CELLUZYME® (fungal enzyme), and CISZYME® (monocomponent cellulase), sold by Novo Nordisk Industries A/S. In some embodiments, the enzyme can be stabilized CORONASE® or CORONASE® with 0.75 4-formyl phenyl boronic acid (4-FPBA) available from Novozymes A/S (Copenhagen, Denmark). Also suitable for use in the formulations of the present invention can be blends of two or more of these enzymes which can be produced by many of these manufacturers, for example a protease/lipase blend, a protease/amylase blend, a protease/amylase/lipase blend, and the like. In some embodiments, the enzyme can be an amylase such as STAINZYME® from Novozymes A/S (Copenhagen, Denmark). In some embodiments, the enzyme can be an amylase such as PREFERENZ™ from DuPont (Wilmington, Del.). In some embodiments, the formulations can include a mannan stain remover such as MANNAWAY® (Novozymes, Copenhagen, Denmark).

The enzyme can be added in any appropriate amount suitable to achieve its intended purpose. But in certain embodiments, the enzyme can be present from about 0.5% to about 1.5% by weight of the formulation, and in certain embodiments at about 0.75% by weight of the formulation.

The formulation disclosed herein can also include a defoamer. In certain embodiments, the defoamer can be a salt of coconut oil fatty acid (also referred to as coconut fatty acid or dodecanoic acid). In particular embodiments, the defoamer is the sodium salt of coconut oil fatty acid. In some embodiments, the salt of coconut oil fatty acid can be present from about 0.1% to about 5% by weight of the formulation, from about 0.1% to about 4% by weight of the formulation, from about 0.1% to about 3% by weight of the formulation, from about 0.1% to about 2.5% by weight of the formulation, from about 0.1% to about 2% by weight of the formulation, from about 0.1% to about 1.5% by weight of the formulation, from about 0.1% to about 1% by weight of the formulation. In other embodiments, the coconut oil fatty acid can be present at about 0.1%, 0.2%, 0.3%, 0.4%, 0.5%, 0.6%, 0.7%, 0.8%, 0.9%, or 1% by weight of the formulation.

In other embodiments, the defoamer can be an organosiloxane-type defoamer, such as any of the defoaming agents disclosed and described in U.S. Patent Application Publication No. 2013/0326823, U.S. Patent Application Publication No. 2013/0327364, U.S. Patent Application Publication No. 2014/0023609, and U.S. Patent Application Publication No. 2014/0352076, each of which is incorporated herein by reference in its entirety.

In some embodiments, the formulation can comprise at least one anti-redeposition agent. In some embodiments, the anti-redeposition agent can be an anti-redeposition polymer. In some embodiments, the anti-redeposition agent can be an acrylic acid polymer, an acrylic acid/maleic acid copolymer, an acrylic acid/methacrylic acid copolymer, or a carboxylate polyelectrolyte copolymer. In some embodiment, the anti-redeposition agent can be an acrylic polymer selected from SOKALAN PA 30, SOKALAN PA 20, SOKALAN PA 15, and SOKALAN CP 10 (BASF GmbH, Germany) and ACUSOL 445G and ACUSOL 445N (The Dow Chemical Company, Midland, Mich.). In some embodiments, the anti-redeposition agent can be an acrylic acid/maleic acid copolymer selected from ACUSOL 460N and ACUSOL 505N (The Dow Chemical Company, Midland, Mich.) and SOKALAN CP 5, SOKALAN CP 45, and SOKALAN CP 7 (BASF GmbH, Germany). In some embodiments, the anti-redeposition agent can be an acrylic/methacrylic copolymer. In some embodiments, the anti-redeposition agent can be an anionic polymer selected from ALCOSPERSE 725 and ALCOSPERSE 747 (Alco Chemical, Chattanooga, Tenn.) and ACUSOL 480N (The Dow Chemical Company, Midland, Mich.). In some embodiments, the anti-redeposition agent can be ACUSOL 445G (The Dow Chemical Company, Midland, Mich.). In some embodiments, the anti-redeposition agent can be ACUSOL 445N (The Dow Chemical Company, Midland, Mich.). In some embodiments, the anti-redeposition agent can be ALCOSPERSE 747. In some embodiments, the anti-redeposition agent can be DEQUEST SPE 1202 (Italmatch Chemicals, Genova, Italy). In some embodiments, the anti-redeposition polymer can be SOKALAN HP 20 (BASF, Germany) an ethoxylated polyethylene imine.

In some embodiments, the anti-redeposition agent can be an acrylic homopolymer having an average molecular weight between 3,000 and 6,000. In some embodiments, the anti-redeposition agent can be an acrylic homopolymer having an average molecular weight of about 4,500.

In some embodiments, the anti-redeposition agent can be an acrylic/styrene copolymer having an average molecular weight between 1,500 and 6,000. In some embodiments, the anti-redeposition agent can be an acrylic/styrene copolymer having an average molecular weight of about 3,000.

In some embodiments, the formulation can comprise from about 0.01% to about 5%, from about 0.01% to about 2.5%, from about 0.01% to about 1%, from about 0.01% to about 0.5%, from about 0.1% to about 0.4%, from about 0.1% to about 0.3%, or from about 0.15% to about 0.3% by weight of the anti-redeposition agent. In other embodiments, the formulation can comprise about 0.25% by weight of the anti-redeposition agent.

The formulations described herein can further include one or more shading dyes. Suitable shading dyes can include chromophore types including, but not limited to, azo, anthraquinone, triarylmethane, methine quinophthalone, azine, oxazine, and thiazine, which may be of any desired color, hue, or shade. Suitable shading dyes can be obtained from many major suppliers such as Clariant, Dystar, Avecia, BASF, Milliken, and Bayer. In some embodiments, the shading dye can be LIQUITINT blue HP dye. In some embodiments, the shading dye can be disperse violet 28 (DV28). In other embodiments, however, the formulations disclosed herein can be completely or substantially shading dye-free.

The formulations disclosed herein can optionally include one or more perfumes or fragrances. As used herein, the term "perfume" can be used in its ordinary sense to refer to, and include, any fragrant substance or mixture of substances including natural (obtained by extraction of flowers, herbs, leaves, roots, barks, wood, blossoms, or plants), artificial (mixture of natural oils or oil constituents), and synthetically produced odoriferous substances. Typically, perfumes can be complex mixtures of blends of various organic compounds such as alcohols, aldehydes, ethers, aromatic compounds and varying amounts of essential oils (e.g., terpenes) such as from 0% to 80%, usually from 1% to 70% by weight, of the essential oils themselves—being volatile odoriferous compounds and also serving to dissolve the other components of the perfume. Suitable perfume ingredients include those disclosed in "Perfume and Flavour Chemicals (Aroma Chemicals)", published by Steffen Arctander (1969), which can be incorporated herein by reference. In some embodiments, the perfume can be lavender. To the extent a perfume is included in a given formulation, from about 0.01% to about 5% by weight of the perfume can be included. In certain embodiments, about 0.75 weight percent perfume can be included in the formulation. In other embodiments, however, the formulation can be completely or substantially free of perfumes.

In some embodiments, the fragrance can be encapsulated in, for example, water-insoluble shell, microcapsule, nanocapsule or any combination thereof. Examples of encapsulated fragrance are known in the art, for example, U.S. Pat. Nos. 6,194,375, 8,426,353, and 6,024,943, each of which is herein incorporated by reference in their entireties.

In other embodiments, the formulations can include one or more soil-releasing polymers. Suitable soil-releasing polymers include, but are not limited to, TEXCARE SRN—a nonionic polyester of polypropylene terephthalate (Clariant); REPEL-O-TEX SRP—a polyethylene glycol polyester (Solvay); end-capped and non-end-capped sulfonated and unsulfonated PET/POET polymers of the type disclosed in WO 2010/069957 and WO 1995/032997; polyethylene glycol/polyvinyl alcohol graft copolymers such as SOKALAN HP 22 (BASF, Germany); and anionic hydrophobic polysaccharides of the type disclosed in U.S. Pat. No. 6,764,992. Each of the patent publications noted in this paragraph are incorporated herein by reference in their entirety.

In some embodiments, the formulations can include up to about 3 weight percent of the soil-releasing polymer. In other embodiments, the formulation can include up to about 2 weight percent of the soil-releasing polymer. And in still further embodiments, the formulation can include about 1% by weight of the soil-releasing polymer.

In some embodiments, the formulations can comprise a bittering agent such as denatonium benzoate, sold under the trade name of BITREX® (Johnson Matthey, London, United Kingdom).

The formulations herein may further include one or more preservatives, such as ROCIMA 586 (a mixture of 5-Chloro-2-methyl-4-isothiazolin-3-one (CMIT), 2-Methyl-4-isothiazolin-3-one (MIT), and 2-Bromo-2-nitropropane-1,3-diol (bronopol) sold by The Dow Chemical Company, Midland, Mich.) and/or ACTICIDE CBM2 (a mixture of 5-chloro-2-methyl-4-isothiazolin-3-one, 2-methyl-4-isothiazolin-3-one, and 1,2-benzisothiazolin-3-one, manufactured by THOR GmbH, Speyer, Germany.

EXAMPLES

The formulations described herein are now further detailed with reference to the following examples. These examples are provided for the purpose of illustration only and the embodiments described herein should in no way be construed as being limited to these examples. Rather, the embodiments should be construed to encompass any and all variations which become evident as a result of the teaching provided herein.

Example 1: General Test Procedures

1. Zein Test

The test surfactant solution can be a solution with 3% active surfactant, or a 10% dilution of a surfactant formulation/product which has a total surfactant concentration of about 10%-25%. Zein protein was added to an appropriate amount of the test surfactant solution so that some solids remained undissolved. The mixture was stirred for one hour. Undissolved Zein was then removed by filtration. A 3 mL aliquot of the filtered denatured solution was then analyzed for the weight of solids by drying the solution in an oven at 70° C. The weight of solids in a 3 mL aliquot of the test surfactant solution (in the absence of Zein) was also measured by drying the solution. The quantity of dissolved Zein in the Zein/surfactant solution was then calculated by difference and reported as g Zein/100 g surfactant solution (also called "% Zein" or "Zein score").

Alternatively, undissolved Zein can be removed by filtration and undissolved solids are measured gravimetrically. The amount of dissolved Zein remaining in the filtrate is calculated by difference, and reported as g Zein/100 g surfactant solution. In a comparative study, the lower the dissolved Zein, the milder the product.

2. Corneosurfametry Test

The test surfactant solution can be a solution with 3% active surfactant, or a 10% dilution of a surfactant formulation/product which has a total surfactant concentration of about 10%-25%. Corneosurfametry involves removing a few layers of human skin from the volar forearm of healthy adults using skin surface strippings. The skin was collected with D-Squame tapes (for tests with neutral pH formulas) and with Book tape (for tests with high pH formulas). The tapes were then soaked in the test surfactant solutions for 10 minutes. The tapes were then dried and stained with fuchian dyes for 3 minutes. Once the tapes are dry, they were analyzed with spectrophotometer. CSM L*-C* data were obtained. In a comparative study, the higher the CSM L*-C*, the less damaged the skin.

3. In Vitro Cytokine Release Test

The test surfactant solution can be 3% dilution of a surfactant formulation/product which has a total surfactant concentration of about 10%-25%. The EpiDerm™ Skin Model provided by MatTek Corporation was used in this test. The target cells were epithelial, derived from human skin. The test surfactant solutions were applied directly to the tissue culture surface, at the air interface, to determine the effect of the surfactant solutions on release of pro-inflammatory cytokines. Where tissue viability was not decreased by 50% as compared to the negative control tissue (as measured by MTT reduction), the inflammatory potential was then measured by the production of the cytokines IL-1α and/or IL-1ra.

In the treatment phase six skin equivalents were used for each test solution, and individual results were averaged to provide an overall response. An aliquot of 100 µl of the test solution was applied to each skin equivalent for 1 hour exposure time followed by 5 rinses of Ca and Mg free phosphate buffered saline (PBS) solution. Each tissue was placed in a 6 well tray with assay medium for each rinse and returned to incubation for 24 hours. Following incubation tissues were assessed for cytokine responses of IL-1α and IL-1ra. In a comparative study, the lower the cytokine score, the less irritating the product.

Example 2. Composite or Detergent Mildness Indicator

For each product, the Zein solubilized percentage was measured on 3 replicates, the corneosurfametry (CSM) L*-C* was measured on 24 replicates, and levels of cytokines IL-1α and IL-1ra were measured on 3 replicates.

The Zein, CSM and cytokine values were summarized for each product by computing the average across replicates. Since the units and magnitudes vary across these measurements, standardized scores for each measure were calculated in order to create a composite score. The standardized score for a particular product was calculated by taking the difference between the product's observed measure and the overall sample mean and then dividing by the sample standard deviation. In order to be consistent that lower scores indicate a milder product, the reverse sign was used for the standardized CSM measure.

The overall raw mildness score for a composite mildness indicator was calculated as the sum of the standardized Zein, CSM and cytokine values IL-1α values. By giving the same weight to each measure, this composite score that each of the measures are equally important.

To better measure the mildness of each product, bootstrap mildness index may be used. The bootstrap mildness index can be obtained by a nonparametric bootstrap procedure. To do so, 95% confidence intervals were constructed and values from the observed replicates were randomly sampled with replacement and the mildness indices were computed based on this bootstrapped data. This process was repeated and the 2.5 and 97.5 percentiles of the bootstrap mildness index were taken to be the confidence limits.

Example 3: Surfactant Formulations

TABLE 1

| Formulation | AES (wt %) | LAS (wt %) | Nonionic surfactant (wt %) | Co-surfactant | Co-surfactant type |
|---|---|---|---|---|---|
| 1 | 10 | 0 | 10 | 0 | N/A |
| 2 | 5.7 | 0 | 11.4 | 2.85 | APG |
| 3 | 10.52 | 0 | 6.33 | 3.15 | APG |
| 4 | 9.1 | 0 | 10.92 | 0 | N/A |
| 5 | 4.8 | 3.2 | 9.6 | 2.4 | CAPB |
| 6 | 6.31 | 4.21 | 6.31 | 3.16 | APG |
| 7 | 8 | 0 | 9.6 | 2.4 | CAPB |
| 8 | 6.67 | 0 | 13.33 | 0 | N/A |
| 9 | 8 | 0 | 8 | 4 | CAPB |
| 10 | 8 | 0 | 8 | 4 | High Ethoxylation |
| 11 | 8 | 0 | 9.6 | 2.4 | High Ethoxylation |
| 12 | 4.8 | 3.2 | 9.6 | 2.4 | High Ethoxylation |
| 13 | 7.5 | 5 | 7.5 | 0 | N/A |
| 14 | 10 | 4 | 6 | 0 | N/A |

Surfactant formulations were prepared according to weight percentages shown in Table 1. The total surfactant concentration was 20 wt %. The same surfactant ratio can be used for formulations at a different concentration, e.g., from 5 wt %-30 wt %.

Nonionic surfactant used here was an alcohol ethoxylate. AES used here was alcohol ethoxysulfate 3EO.

In addition, the surfactant formulations contained citric acid, NaOH, triethanolamine, and cocofatty acid.

Example 4: Comparative Zein Score Study

Zein scores for Formulations 1-12 (tested as a 10% dilution) were obtained using the procedures described in Example 1. These formulations were significantly milder than the commercial laundry detergent (Product 11), which is claimed to be mild (tested as a 10% dilution). (Table 2).

TABLE 2

| Formulation | % Zein solubilized (g/100 g surfactant solution) |
|---|---|
| PRODUCT 11 | 3.9 |
| 1 | 2.5 |
| 2 | 1 |
| 3 | 2.5 |
| 4 | 2.3 |
| 5 | 2.1 |
| 6 | 1.9 |

TABLE 2-continued

| Formulation | % Zein solubilized (g/100 g surfactant solution) |
| --- | --- |
| 7 | 2.6 |
| 8 | 1.7 |
| 9 | 1.8 |
| 10 | 2.2 |
| 11 | 1.9 |
| 12 | 2.6 |

Example 5: Comparative In Vitro Cytokine Release Study

In vitro cytokine release values for Formulations 1-12 (tested as a 3% dilution) were obtained using the procedures described in Example 1.

Interpretation of these results was less clear. In some cases formulas show a high 1L-1a cytokine value yet a low 1L-1rα cytokine value; see for example formula 12 which has one of the highest 1L-1α score (72.54), yet one of the lowest 1L-1rα score (3912), while formula 3 has a low to medium 1L-1α score (58.9) yet one of the highest 1L-1rα score (5315). It was therefore the purpose of this invention to combine all testing into a single value called the detergent mildness index (DMI), which is explained in detail in this patent. (Table 3).

TABLE 3

| Formulation | IL-1α Cytokine (pg/mL) | IL-1ra Cytokine (pg/mL) |
| --- | --- | --- |
| PRODUCT 11 | 90.74 | 3563.04 |
| 1 | 41.81 | 4370.48 |
| 2 | 48.3 | 4008.15 |
| 3 | 58.9 | 5315.87 |
| 4 | 41.32 | 3775.24 |
| 5 | 75.06 | 5579.76 |
| 6 | 100.16 | 6167.9 |
| 7 | 42.08 | 3835.52 |
| 8 | 61.01 | 4797.23 |
| 9 | 66.35 | 3430.69 |
| 10 | 59.61 | 3294.44 |
| 11 | 49.41 | 2849.1 |
| 12 | 72.54 | 3912.04 |

Example 6: Comparative Corneosurfametry Study

Corneosurfametry test was performed for Formulations 2, 4, and 8 (tested as a 10% dilution), along with water, 1% SDS, and a competitive benchmark mild laundry detergent.

Formulations 2, 4, and 8 are significantly milder than Product 11 (tested as a 10% dilution). (Table 4).

TABLE 4

| Formulation | CIM |
| --- | --- |
| PRODUCT 11 | 54.54 |
| Water | 74.11 |
| 1% SDS | 36.84 |
| 2 | 71.32 |
| 4 | 69.64 |
| 8 | 71.72 |

Example 7: Comparative Cleaning Performance

Formulations 1-12 were tested for their cleaning performance. The reference formulation is the combination 'Free Clear' surfactant chassis benchmark (containing 4% LAS, 8% nonionic surfactant, 8% AES, and sodium citrate). The wash test consisted of 2 washes in a traditional top-loaded washing machine at both 90° F. and 59° F. using all 8 stains (Grass, Mud, Grape Juice, Coffee, BBQ sauce, Chocolate Ice Cream, Dust Sebum, blood) in 120 ppm water on two fabrics (woven blend and knitted cotton). The average performance of the surfactant formulations were rated by Least Square mean. The cleaning performance combined all of the cleaning data from both temperatures, fabrics and all stains to reflect an overall cleaning value. The data indicates that the cleaning performance of the mild surfactant formulations are comparable to the reference formulation when modeled in JMP software program. The overall cleaning scores are listed in Table 5.

TABLE 5

| Formulation | Overall Cleaning Score |
| --- | --- |
| Reference formulation | 56.223 |
| 1 | 57.31 |
| 2 | 57.04 |
| 3 | 55.517 |
| 4 | 56.175 |
| 5 | 55.04 |
| 6 | 57.46 |
| 7 | 54.98 |
| 8 | 55.9 |
| 9 | 55.74 |
| 10 | 56.72 |
| 11 | 57.26 |
| 12 | 56.61 |

Example 8: Detergent Mildness Indicator

Detergent mildness indicators were calculated based on combining the standardized results from Zein test and total cytokine release test as described in Example 2. DMI is the preferred method for showing the mildness of detergent products. However, partial-DMI, as defined previously, may also be calculated to indicate relative mildness of detergent products, as shown in Table 6.

Formulations 1-12 were shown as mild with a Partial-DMI of −0.54 or below. (Table 6). Formulations 13 and 14 are much harsher with a Partial-DMI being 3.06 and 3.75, respectively. Formula 13 is a control formula comprised of wt fractions.

TABLE 6

| Formulation | Weight Fraction of AES* | Weight Fraction of LAS* | Weight Fraction of Nonionic* | Weight Fraction of Co-surfactant* | Co-surfactant Type | Partial DMI Mildness Indicator |
|---|---|---|---|---|---|---|
| | (Total surfactant concentration 20%) | | | | | |
| 1 | 0.5 | 0 | 0.5 | 0 | N/A | −1.44 |
| 2 | 0.285 | 0 | 0.57 | 0.1425 | APG | −3.30 |
| 3 | 0.526 | 0 | 0.3165 | 0.1575 | APG | −0.98 |
| 4 | 0.455 | 0 | 0.546 | 0 | N/A | −1.92 |
| 5 | 0.24 | 0.16 | 0.48 | 0.12 | CAPB | −0.96 |
| 6 | 0.3155 | 0.2105 | 0.3155 | 0.158 | APG | −0.54 |
| 7 | 0.40 | 0 | 0.48 | 0.12 | CAPB | −1.55 |
| 8 | 0.3335 | 0 | 0.6665 | 0 | N/A | −1.98 |
| 9 | 0.40 | 0 | 0.40 | 0.20 | CAPB | −2.09 |
| 10 | 0.40 | 0 | 0.40 | 0.20 | High Ethoxylation | −1.73 |
| 11 | 0.40 | 0 | 0.48 | 0.12 | High Ethoxylation | −2.40 |
| 12 | 0.24 | 0.16 | 0.48 | 0.12 | High Ethoxylation | −0.78 |
| 13 | 0.375 | 0.25 | 0.375 | 0 | N/A | 3.06 |
| 14 | 0.50 | 0.20 | 0.30 | 0 | N/A | 3.75 |

*The term "weight fraction" has been defined earlier.
*Partial-DMI is a mildness indicator calculated based on standardized Zein scores and standardized total cytokine values.

Example 9: Comparison with Existing Marketed Products

1. Products and Individual Tests

Formulation A was prepared based on the surfactant composition of Formula 8 discussed above but with a total surfactant concentration at 18 wt %. The ingredients and their amounts of Formulation A are listed in Table 7.

TABLE 7

| Material Description | Amount (wt %) |
|---|---|
| Deionized Water | 78.11 |
| C12-C15 Alcohol Ethoxylate 7EO | 12.0 |
| Alcohol Ethoxysulfate 3EO | 6.0 |
| Sodium Carbonate | 2.25 |
| Chelating Agent | 0.5 |
| Fragrance | 0.4 |
| Sodium Cocoate | 0.28 |
| Sodium Methylacrylate Styrene Copolymer | 0.25 |
| Diaminostilbene disulfonate | 0.18 |
| Preservative | 0.03 |
| Grand Total | 100.0 |

Formulation A's mildness was compared to existing marketed products (e.g., PRODUCTS 1-13). Two drivers of cleaning are surfactant level and enzyme content. Surfactant level and enzyme status of formulas are captured in Table 8. Full DMI Mildness data for these formulas are captured in Table 9.

TABLE 8

| Product | wt % Surfactant | Contains enzymes? |
|---|---|---|
| Formulation A | 18% | N |
| PRODUCT 1 | 10%-11% | N |
| PRODUCT 2 | 10%-11% | N |
| PRODUCT 3 | 10%-11% | N |
| PRODUCT 4 | 20% | N |
| PRODUCT 5 | 10%-11% | N |
| PRODUCT 6 | 15% | Y |
| PRODUCT 7 | 20% | N |
| PRODUCT 8 | 20%-24% | |
| PRODUCT 9 | 20%-24% | |
| PRODUCT 10 | 24% | Y |
| PRODUCT 11 | 24% | Y |
| PRODUCT 12 | 37% | Y |
| PRODUCT 13 | | Y |

For each product the Zein solubilized percentage was measured on 3 replicates, the corneosurfametry (CSM) L*-C* was measured on 24 replicates, and levels of cytokines IL-1α and IL-1ra were measured on 3 replicates. In addition, the ratio and log-ratio of IL-1ra to IL-1α for each replicate were computed.

Zein test was conducted with 10% dilution of Formulation A and 12 marketed products without correction for active surfactants, using the procedures describe in Example 1. The results are shown in FIG. 1. Formulation A provided a lower Zein score than all 12 marketed products.

Corneosurfametry test was conducted with 10% dilution of Formulation A and 13 marketed products without correction for active surfactants, along with water and 1% SDS, using the procedures describe in Example 1. The results are shown in FIG. 2. Corneosurfametry test was repeated with 10% solutions of Formulation A and 7 marketed products without correction for active surfactants, and the results are shown in FIG. 3. Formulation A provided a higher CSM value compared to the marketed products.

In vitro cytokine release test was conducted with 3% dilution of Formulation A and 11 marketed products, using the procedures described in Example 1. The results for cytokine IL-1α and IL-1ra are shown in FIG. 4 and FIG. 5, respectively. Formulation A provided a lower cytokine release levels for both IL-1α and IL-1ra as compared to the marketed products.

The Zein, CSM and cytokine values were summarized for each product by computing the average across replicates. The observed values of Zein test, Corneosurfametry test, and In vitro cytokine release test are listed in Table 9.

TABLE 9

| Product | Zein score | CSM L*-C* | Cytokine IL-1α | Cytokine IL-1ra |
|---|---|---|---|---|
| Formulation A | 1.3 | 54.9 | 77.3 | 8,049.7 |
| PRODUCT 1 | 1.6 | 51.4 | 182.7 | 11,800.4 |
| PRODUCT 2 | 2.0 | 51.4 | 165.4 | 14,709.9 |
| PRODUCT 3 | 1.3 | 51.9 | 517.5 | 53,309.3 |
| PRODUCT 4 | 3.2 | 53.5 | 326.6 | 21,462.2 |
| PRODUCT 5 | 2.0 | 50.4 | 200.9 | 14,123.1 |
| PRODUCT 6 | 2.3 | 51.5 | 499.2 | 14,840.8 |
| PRODUCT 7 | 2.2 | 51.3 | 743.6 | 70,901.2 |
| PRODUCT 8 | 2.7 | 51.5 | 578.5 | 28,710.6 |
| PRODUCT 9 | 3.0 | 51.4 | 622.5 | 19,171.2 |
| PRODUCT 10 | 3.4 | 51.3 | 744.9 | 22,659.6 |
| PRODUCT 11 | 3.6 | 48.9 | 1,083.6 | 49,547.0 |

2. Composite/Detergent Mildness Indicator

Since the units and magnitudes vary across the Zein, CSM, and cytokine measurements, standardized scores for each measure were calculated in order to create a composite score. The standardized score for a particular product was calculated by taking the difference between the product's observed measure and the overall sample mean and then dividing by the sample standard deviation. Furthermore, Bootstrapped mildness values were obtained in accordance with the nonparamatric bootstrap procedure as described before.

Calculated Mildness (i.e., DMI) and Bootstrap mildness data are listed in Tables 10A-10E. Tables 10A through 10E are different ways to calculate DMI. All calculations show that formula A is milder than any of the commercial products. The preferred method to calculate DMI is the equation shown in Table 10A, which is the sum of standardized Zein+ standardized cytokine 1L-1α+ standardized CSM. One competitive product in the data set is the PRODUCT 4 formula. According to Table 10A, formula A is between 4.1 and 3.3 units lower in DMI value compared to PRODUCT 4 (using lower and upper bound bootstrap data). The next mildest product is PRODUCT 1 which is between 2.9 and 3.2 units lower than PRODUCT 4. Thus, the inventive formula is unique in that it is 3.3 units lower than PRODUCT 4. Going back to Table 6, the composition of PRODUCT 4 is Formula 14 and the composition of Formula A is Formula 8. Other products from Table 6 with a mildness score lower than formula 8 are formulas 2, 9, and 11. We can conclude that the composition of a formula that is uniquely milder than commercial products has a composition with weight fractions of 0.0 LAS, 0.40 or lower AES, and the remainder nonionic and/or co-surfactants that are high ethoxylation nonionic, CAPB and/or APG.

TABLE 10A

| Zein + IL-1α + CSM L*-C* | Calculated DMI Mildness | Bootstrap Mean Mildness | Bootstrap Lower Bound Mildness | Bootstrap Upper Bound Mildness |
|---|---|---|---|---|
| Formulation A | -5.0 | -4.8 | -5.3 | -4.4 |
| PRODUCT 1 | -1.8 | -1.8 | -2.4 | -1.2 |
| PRODUCT 2 | -1.4 | -1.4 | -2.0 | -0.7 |
| PRODUCT 3 | -1.4 | -1.4 | -2.1 | -0.6 |
| PRODUCT 4 | -0.7 | -0.6 | -1.2 | 0.1 |
| PRODUCT 5 | -0.6 | -0.7 | -1.3 | 0.0 |
| PRODUCT 6 | 0.0 | 0.0 | -0.8 | 0.9 |
| PRODUCT 7 | 0.8 | 0.8 | -0.1 | 1.7 |
| PRODUCT 8 | 0.9 | 0.9 | -0.1 | 1.8 |
| PRODUCT 9 | 1.4 | 1.4 | 0.3 | 2.5 |
| PRODUCT 10 | 2.4 | 2.3 | 1.3 | 3.3 |
| PRODUCT 11 | 5.4 | 5.1 | 4.1 | 6.0 |

TABLE 10B

| Zein + (IL-1α + IL-1ra) + CSM L*-C* | Observed Mildness | Bootstrap Mean Mildness | Bootstrap Lower Bound Mildness | Bootstrap Upper Bound Mildness |
|---|---|---|---|---|
| Formulation A | -4.9 | -4.8 | -5.2 | -4.3 |
| PRODUCT 1 | -1.8 | -1.8 | -2.3 | -1.2 |
| PRODUCT 2 | -1.3 | -1.3 | -1.9 | -0.6 |
| PRODUCT 3 | -0.7 | -0.7 | -1.5 | 0.1 |
| PRODUCT 4 | -0.6 | -0.5 | -1.2 | 0.1 |
| PRODUCT 5 | -0.6 | -0.6 | -1.2 | 0.0 |
| PRODUCT 6 | -0.3 | -0.3 | -1.1 | 0.5 |
| PRODUCT 7 | 1.6 | 1.6 | 0.8 | 2.5 |
| PRODUCT 8 | 0.8 | 0.8 | -0.1 | 1.6 |
| PRODUCT 9 | 1.0 | 1.0 | -0.1 | 2.1 |
| PRODUCT 10 | 1.8 | 1.8 | 1.0 | 2.7 |
| PRODUCT 11 | 5.1 | 4.9 | 3.9 | 5.6 |

TABLE 10C

| Zein + (IL-1ra/IL-1α) + CSM L*-C* | Observed Mildness | Bootstrap Mean Mildness | Bootstrap Lower Bound Mildness | Bootstrap Upper Bound Mildness |
|---|---|---|---|---|
| Formulation A | -5.0 | -4.7 | -5.8 | -3.5 |
| PRODUCT 1 | -0.9 | -0.9 | -2.4 | 0.2 |
| PRODUCT 2 | -1.3 | -1.2 | -2.6 | 0.1 |
| PRODUCT 3 | -2.8 | -2.7 | -3.7 | -1.7 |
| PRODUCT 4 | -0.2 | -0.1 | -1.5 | 1.0 |
| PRODUCT 5 | 0.2 | 0.0 | -1.6 | 1.3 |
| PRODUCT 6 | 1.2 | 1.1 | 0.2 | 2.0 |
| PRODUCT 7 | -1.2 | -1.0 | -2.0 | 0.0 |
| PRODUCT 8 | 1.0 | 1.0 | -0.1 | 2.0 |
| PRODUCT 9 | 2.1 | 2.0 | 1.0 | 3.2 |
| PRODUCT 10 | 2.9 | 2.6 | 1.7 | 3.4 |
| PRODUCT 11 | 3.9 | 3.8 | 2.8 | 4.6 |

TABLE 10D

| Zein + Log(IL-1ra/IL-1α) + CSM L*-C* | Observed Mildness | Bootstrap Mean Mildness | Bootstrap Lower Bound Mildness | Bootstrap Upper Bound Mildness |
|---|---|---|---|---|
| Formulation A | -4.8 | -4.6 | -5.4 | -3.7 |
| PRODUCT 1 | -1.1 | -1.0 | -2.2 | 0.2 |
| PRODUCT 2 | -1.3 | -1.2 | -2.2 | -0.1 |
| PRODUCT 3 | -2.6 | -2.6 | -3.4 | -1.7 |
| PRODUCT 4 | -0.4 | -0.3 | -1.4 | 0.9 |
| PRODUCT 5 | 0.0 | 0.0 | -1.3 | 1.3 |
| PRODUCT 6 | 1.2 | 1.3 | 0.3 | 2.2 |
| PRODUCT 7 | -1.1 | -1.0 | -1.9 | -0.1 |
| PRODUCT 8 | 0.8 | 0.9 | -0.3 | 1.9 |
| PRODUCT 9 | 2.2 | 2.2 | 1.1 | 3.3 |
| PRODUCT 10 | 3.3 | 2.7 | 1.6 | 3.7 |
| PRODUCT 11 | 3.7 | 3.7 | 2.6 | 4.5 |

TABLE 10E

| Zein + (IL-1α/IL-1ra) + CSM L*-C* | Observed Mildness | Bootstrap Mean Mildness | Bootstrap Lower Bound Mildness | Bootstrap Upper Bound Mildness |
|---|---|---|---|---|
| Formulation A | −4.5 | −4.4 | −5.0 | −3.8 |
| PRODUCT 1 | −1.2 | −1.1 | −2.1 | 0.1 |
| PRODUCT 2 | −1.1 | −1.1 | −1.9 | −0.3 |
| PRODUCT 3 | −2.4 | −2.4 | −3.2 | −1.6 |
| PRODUCT 4 | −0.6 | −0.4 | −1.3 | 0.8 |
| PRODUCT 5 | −0.1 | −0.1 | −1.1 | 1.2 |
| PRODUCT 6 | 1.1 | 1.4 | 0.2 | 2.6 |
| PRODUCT 7 | −0.9 | −0.9 | −1.8 | −0.1 |
| PRODUCT 8 | 0.5 | 0.7 | −0.4 | 1.8 |
| PRODUCT 9 | 2.0 | 2.3 | 1.0 | 3.5 |
| PRODUCT 10 | 3.8 | 2.8 | 1.4 | 4.1 |
| PRODUCT 11 | 3.5 | 3.5 | 2.4 | 4.4 |

The standardized values of the Zein, CSM, and cytokine values are shown in Tables 11A and 11B.

TABLE 11A

| Product | Standardized Zein score | Standardized CSM L*-C* | Standardized Cytokine IL-1α | Standardized Cytokine IL-1ra |
|---|---|---|---|---|
| Formulation A | −1.4 | −2.3 | −1.3 | −1.0 |
| PRODUCT 1 | −0.9 | 0.1 | −1.0 | −0.8 |
| PRODUCT 2 | −0.5 | 0.1 | −1.0 | −0.6 |
| PRODUCT 3 | −1.3 | −0.2 | 0.1 | 1.3 |
| PRODUCT 4 | 1.1 | −1.3 | −0.5 | −0.3 |
| PRODUCT 5 | −0.5 | 0.9 | −0.9 | −0.7 |
| PRODUCT 6 | −0.1 | 0.1 | 0.1 | −0.6 |
| PRODUCT 7 | −0.3 | 0.2 | 0.9 | 2.2 |
| PRODUCT 8 | 0.5 | 0.1 | 0.3 | 0.1 |
| PRODUCT 9 | 0.8 | 0.1 | 0.5 | −0.4 |
| PRODUCT 10 | 1.3 | 0.2 | 0.9 | −0.2 |
| PRODUCT 11 | 1.5 | 1.8 | 2.0 | 1.1 |

TABLE 11B

| Product | (IL-1α + IL-1ra) | IL-1α/IL-1ra | Log(IL-1α/IL-1ra) | IL-1ra/IL-1α |
|---|---|---|---|---|
| Formulation A | −1.3 | −0.9 | −1.1 | −1.3 |
| PRODUCT 1 | −1.0 | −0.4 | −0.3 | −0.1 |
| PRODUCT 2 | −0.9 | −0.8 | −0.9 | −1.0 |
| PRODUCT 3 | 0.8 | −0.9 | −1.1 | −1.3 |
| PRODUCT 4 | −0.4 | −0.4 | −0.2 | 0.0 |
| PRODUCT 5 | −0.9 | −0.5 | −0.3 | −0.1 |
| PRODUCT 6 | −0.3 | 1.1 | 1.3 | 1.2 |
| PRODUCT 7 | 1.7 | −0.8 | −1.0 | −1.1 |
| PRODUCT 8 | 0.2 | 0.0 | 0.2 | 0.4 |
| PRODUCT 9 | 0.0 | 1.1 | 1.2 | 1.2 |
| PRODUCT 10 | 0.4 | 2.3 | 1.8 | 1.4 |
| PRODUCT 11 | 1.7 | 0.1 | 0.4 | 0.6 |

Five composite mildness indicators were computed for Formulation A and 11 marketed products, as described in Example 2. The numbers are listed in Table 12, and also plotted in FIGS. 6-10. Formulation A is clearly milder than the 11 marketed products, regardless of the method used to calculate CMI. Table 12 shows five CMI calculations.

TABLE 12

| Product | Zein + IL-1α + CSM | Zein + (IL-1α + IL-1ra) + CSM | Zein + (IL-1ra/IL-1α) + CSM | Zein + (IL-1α/IL-1ra) + CSM | Zein + Log(IL-1α/IL-1ra) + CSM |
|---|---|---|---|---|---|
| Formulation A | −5.0 | −4.9 | −5.0 | −4.5 | −4.8 |
| PRODUCT 1 | −1.8 | −1.8 | −0.9 | −1.2 | −1.1 |
| PRODUCT 2 | −1.4 | −1.3 | −1.3 | −1.1 | −1.3 |
| PRODUCT 3 | −1.4 | −0.7 | −2.8 | −2.4 | −2.6 |
| PRODUCT 4 | −0.7 | −0.6 | −0.2 | −0.6 | −0.4 |
| PRODUCT 5 | −0.6 | −0.6 | 0.2 | −0.1 | 0.0 |
| PRODUCT 6 | 0.0 | −0.3 | 1.2 | 1.1 | 1.2 |
| PRODUCT 7 | 0.8 | 1.6 | −1.2 | −0.9 | −1.1 |
| PRODUCT 8 | 0.9 | 0.8 | 1.0 | 0.5 | 0.8 |
| PRODUCT 9 | 1.4 | 1.0 | 2.1 | 2.0 | 2.2 |
| PRODUCT 10 | 2.4 | 1.8 | 2.9 | 3.8 | 3.3 |
| PRODUCT 11 | 5.4 | 5.1 | 3.9 | 3.5 | 3.7 |

Cleaning performance of Formulation A was also compared with that of marketed products. (Table 13). Formulation A is close to the high tier marketed product in terms of stain removal performance (89.75 and 90.04 vs. 90.47) but has a milder formula. Formulas with composite cleaning of 87.88 are lower tier cleaning. Formulas with composite cleaning of about 87 represent lower tier cleaning products. Formulas with composite cleaning of about 90 represent higher tier cleaning products. Formulation A is comparable to the marketed products in terms of stain removal performance (cleaning score of 89.75 vs. 87.25-90.49 at 59° F.; and cleaning score of 90.04 vs. 87.87-91.04 at 90° F.) but has a milder formula.

TABLE 13

| | Composite cleaning score[1] | |
|---|---|---|
| Product | 59° F. | 90° F. |
| Formulation A | 89.75 | 90.04 |
| PRODUCT 1 | 87.76 | 88.16 |
| PRODUCT 3 | 87.25 | 87.87 |
| PRODUCT 4 | 89.51 | 89.72 |

TABLE 13-continued

| Product | Composite cleaning score[1] | |
|---|---|---|
| | 59° F. | 90° F. |
| PRODUCT 5 | 87.98 | 88.22 |
| PRODUCT 11 | 90.49 | 91.04 |

Having now fully described this invention, it will be understood by those of ordinary skill in the art that the same can be performed within a wide and equivalent range of conditions, formulations and other parameters without affecting the scope of the invention or any embodiment thereof.

[1]Composite cleaning score is obtained by averaging SRI (Stain Removal Index) Values over 5 fabrics (woven cotton, knit cotton, woven blend, polyester, knit blend) and over 8 stains (blood, chocolate ice cream, coffee, dust sebum, grape juice, grass, BBQ sauce, mud).

[2]SRI values averaged over 5 fabrics (woven cotton, knit cotton, woven blend, polyester, knit blend)

Other embodiments of the invention will be apparent to those skilled in the art from consideration of the specification and practice of the invention disclosed herein. It is intended that the specification and examples be considered as exemplary only, with a true scope and spirit of the invention being indicated by the following claim.

What is claimed is:

1. A method for determining a mild aqueous laundry detergent formulation, comprising:
   (i) providing a solution comprising a laundry cleaning effective amount of a surfactant composition,
   (ii) subjecting an appropriate dilution of the solution to Zein test, corneosurfametry test, and in vitro cytokine release test for IL-1α and IL-1ra response, respectively, to obtain a Zein score, a corneosurfametric (CSM) value, and a cytokine release value, and
   (iii) deriving at a detergent mildness indicator (DMI) for each solution based the Zein score, the CSM value, and the cytokine release value.

2. The method of claim 1, wherein
   (i) the Zein test is tested against a 10% dilution of the solution,
   (ii) the corneosurfametric test is tested against a 10% dilution of the solution, and
   (iii) the cytokine release test is tested against a 3% dilution of the solution.

3. The method of claim 1, wherein the DMI is derived from a sum of standardized Zein score, standardized CSM value, and one of standardized cytokine release values, IL-1α, (IL-1α+IL-1ra), (IL-1ra/IL-1α), and $\log_{10}$(IL-1ra/IL-1α), of the solution.

4. The method of claim 1, further comprising a step of comparing the DMIs of two different solutions to determine relative mildness of the solution,
   wherein the lower the DMI, the milder the solution.

5. A method of preparing a mild aqueous laundry detergent formulation, comprising
   (i) providing a solution comprising a laundry cleaning effective amount of a surfactant composition,
   (ii) subjecting an appropriate dilution of the solution to Zein test, corneosurfametry test, and in vitro cytokine release test for IL-1α and IL-1ra response,
   (iii) deriving a detergent mildness indicator (DMI) for the solution from a sum of standardized Zein score, standardized CSM value, and one of standardized cytokine release values, IL-1α, (IL-1α+IL-1ra), (IL-1ra/IL-1α), and $\log_{10}$(IL-1ra/IL-1α), of the solution,
   (iv) comparing the detergent mildness indicator of the solution with that of a reference composition to determine relative mildness of the solution, wherein the lower the DMI, the milder the solution, and
   (v) adding suitable laundry detergent ingredients to the solution to prepare a final mild aqueous laundry detergent formulation, if the solution is milder than the reference composition.

6. The method of claim 5, wherein
   (i) the Zein test is tested against a 10% dilution of the solution,
   (ii) the corneosurfametric test is tested against a 10% dilution of the solution, and
   (iii) the cytokine release test is tested against a 3% dilution of the solution.

7. The method of claim 5, wherein the reference composition comprises 20 wt % reference surfactants based on a total weight of the reference composition, and wherein the reference surfactants consist of an alcohol ethoxysulfate (AES) in an amount of 37.5 wt % based on a total weight of the surfactants, a linear alkylbenzenesulfonate (LAS) in an amount of 25 wt % based on a total weight of the surfactants, and a nonionic surfactant in an amount of 37.5 wt % based on a total weight of the surfactants.

8. The method of claim 5, further comprising a step of adjusting components of the surfactant composition of the solution to adjust its mildness.

9. A mild aqueous laundry detergent formulation comprising from about 15 wt % to about 25 wt % of a surfactant composition based on a total weight of the formulation,
   said formulation having a detergent mildness indicator (DMI) which is at least 3.3 units less than that of a reference detergent composition comprising 20 wt % reference surfactants based on a total weight of the reference detergent composition;
   wherein the detergent mildness indicator is derived from Zein score, CSM value, and one of cytokine release values, IL-1α, (IL-1α+IL-1ra), (IL-1ra/IL-1α), and $\log_{10}$(IL-1ra/IL-1α), of the formulation and of the reference detergent composition; and
   wherein the reference surfactants of the said reference detergent composition consist of an alcohol ethoxysulfate (AES) in an amount of 37.5 wt % based on a total weight of the surfactants, a linear alkylbenzenesulfonate (LAS) in an amount of 25 wt % based on a total weight of the surfactants, and a nonionic surfactant in an amount of 37.5 wt % based on a total weight of the surfactants.

10. The formulation of claim 9, wherein the surfactant composition of the formulation is in an amount of about 20 wt % based on a total weight of the formulation.

11. The formulation of claim 9, wherein the surfactant composition of the formulation comprises a nonionic surfactant, alcohol ethoxysulfate (AES), and optionally a linear alkylbenzenesulfonate (LAS).

12. The formulation of claim 11, wherein the nonionic surfactant of the surfactant composition of the formulation is an alcohol ethoxylate (AE).

13. The formulation of claim 11, wherein the nonionic surfactant of the surfactant composition is present in an amount of from about 30 wt % to about 80 wt % by weight of the surfactant composition.

14. The formulation of claim 11, wherein the alcohol ethoxysulfate (AES) is present in an amount of from about 20% to about 60% by weight of the surfactant composition.

15. The formulation of claim 11, wherein the linear alkylbenzenesulfonate (LAS) is present in an amount of from about 0% to about 25% by weight of the surfactant composition.

16. The formulation of claim 11, wherein the formulation further comprises a co-surfactant selected from the group consisting of a zwitterionic surfactant, a high ethoxylation nonionic surfactant, CAPB, an alkyl polyglucoside (APG), and any combination thereof, wherein the co-surfactant is present in an amount of from about 0.01% to 25% by weight of the surfactant composition.

17. The formulation of claim 16, wherein the surfactant composition of the formulation comprises 40 wt % or less of AES based on a total weight of the surfactant composition, and the remainder of the surfactant composition being alcohol ethoxylate, high ethoxylation alcohol ethoxylate, CAPB, APG, or a combination thereof; and
wherein the surfactants of the formulation comprise no LAS.

18. A mild aqueous laundry detergent formulation comprising from about 5 wt % to about 30 wt % of a surfactant composition based on a total weight of the formulation,
wherein the formulation has at least two of the following characteristics:
(i) the formulation has a Zein score of less than about 3 percent when tested as a 10% dilution,
(ii) the formulation has a corneosurfametric (CSM) value of greater than about 50 when tested as a 10% dilution, and
(iii) the formulation has a cytokine release value of less than about 140 pg/mL IL-1α when tested as a 3% dilution in in vitro cytokine release test.

19. The formulation of claim 18,
wherein the corneosurfametric CSM value of the formulation is at least 1.4 units higher than and the cytokine release value of the formulation is at least 249 pg/mL IL-1α lower than a reference detergent composition; and
wherein the reference detergent composition comprises 20 wt % reference surfactants based on a total weight of the reference detergent composition, and the reference surfactants consist of an alcohol ethoxysulfate (AES) in an amount of 37.5 wt % based on a total weight of the surfactants, a linear alkylbenzenesulfonate (LAS) in an amount of 25 wt % based on a total weight of the surfactants, and a nonionic surfactant in an amount of 37.5 wt % based on a total weight of the surfactants.

20. The formulation of claim 18, wherein a detergent mildness indicator of the formulation is lower than that of a reference formula comprising a surfactant blend of 10.52 wt % AES and 9.48 wt % alcohol ethoxylate, and
wherein the detergent mildness indicator is derived from the sum of Zein score, CSM value, and one of cytokine release values, IL-1α, (IL-1α+IL-1ra), (IL-1ra/IL-1α), and $\log_{10}$(IL-1ra/IL-1α), of the formulation and of the reference detergent composition.

* * * * *

UNITED STATES PATENT AND TRADEMARK OFFICE
CERTIFICATE OF CORRECTION

| | | |
|---|---|---|
| PATENT NO. | : 10,066,190 B2 | Page 1 of 1 |
| APPLICATION NO. | : 15/652845 | |
| DATED | : September 4, 2018 | |
| INVENTOR(S) | : Janet Coope-Epstein et al. | |

It is certified that error appears in the above-identified patent and that said Letters Patent is hereby corrected as shown below:

On the Title Page

Item (72) Inventor's name, add --David Lewin, Venice, FL (US)--.

Signed and Sealed this
Thirtieth Day of April, 2019

Andrei Iancu
*Director of the United States Patent and Trademark Office*